United States Patent [19]

Brunner et al.

[11] Patent Number: 4,698,091

[45] Date of Patent: * Oct. 6, 1987

[54] 2-PHENYLPYRIMIDINES, 2-NAPHTHYLPYRIMIDINES AND 2-HETEROCYCLYLPYRIMIDINES AS SAFENERS FOR PROTECTING CULTIVATED PLANT AGAINST PHYTOTOXIC DAMAGE CAUSED BY HERBICIDES

[75] Inventors: Hans-Georg Brunner, Lausen; Kurt Burdeska; Werner Föry, both of Basel, all of Switzerland

[73] Assignee: Ciba-Geigy Corporation, Ardsley, N.Y.

[*] Notice: The portion of the term of this patent subsequent to Jan. 15, 2001 has been disclaimed.

[21] Appl. No.: 752,475

[22] Filed: Jul. 3, 1985

Related U.S. Application Data

[63] Continuation of Ser. No. 499,603, May 31, 1983, abandoned.

[30] Foreign Application Priority Data

| Jun. 8, 1982 [CH] | Switzerland | 3526/82 |
| Jun. 21, 1982 [CH] | Switzerland | 3795/82 |
| Nov. 16, 1982 [CH] | Switzerland | 6665/82 |

[51] Int. Cl.$^4$ .............. A01N 57/10; A01N 43/48; C07D 239/02
[52] U.S. Cl. .............................. 71/87; 71/88; 71/90; 71/92; 71/93; 544/182; 544/194; 544/211; 544/215; 544/295; 544/296; 544/333; 544/334
[58] Field of Search ............... 544/334, 242, 295, 296, 544/182, 194, 211, 215, 333; 71/87, 88, 90, 92, 93

[56] References Cited

U.S. PATENT DOCUMENTS

| 2,937,171 | 5/1960 | Smith | 544/334 |
| 3,284,188 | 11/1966 | Amagasa | 544/334 |
| 3,442,898 | 5/1969 | Luethi et al. | 260/251 |
| 3,445,466 | 5/1969 | Hahn et al. | 260/251 |
| 3,498,984 | 3/1970 | Santilli et al. | 260/256.5 |
| 3,503,976 | 3/1970 | Reichender et al. | 260/256.4 |
| 3,940,395 | 2/1976 | Santilli et al. | 260/256.5 R |
| 4,084,053 | 4/1978 | Desai et al. | 544/184 |
| 4,297,234 | 10/1981 | Burdeska et al. | 252/301.24 |
| 4,493,726 | 1/1985 | Burdeska et al. | 71/92 |

FOREIGN PATENT DOCUMENTS

| 55693 | 7/1982 | European Pat. Off. . |
| 2202820 | 7/1973 | Fed. Rep. of Germany . |
| 2182994 | 12/1973 | France . |
| 309033 | 7/1930 | United Kingdom . |

OTHER PUBLICATIONS

J. Org. Chem 32 (1967) pp. 1591–1595.
Comptes-rendus Acad AC vol. 281 (1975) pp. 39–41 J. Pankiewics et al.
J. Chem Soc. 1952 pp. 328–333.
Brunner et al, Chem. Abst. 101-191957d.
Hoffmann, Chem. Abst. 79:1350g (1973).
Hagen et al, Chem. Abst. 80:14955d.
Burdeska et al, Chem. Abst. 97:158036d.
Brunner et al, Chem. Abst. 100:156636f.
Sokolova et al, Chem. Abst. 92:15521u.

*Primary Examiner*—Donald G. Daus
*Assistant Examiner*—Cecilia Shen
*Attorney, Agent, or Firm*—Edward McC. Roberts

[57] ABSTRACT

The 2-phenylpyrimidines, 2-naphthylpyrimidines and 2-heterocyclylpyrimidines of the formula I

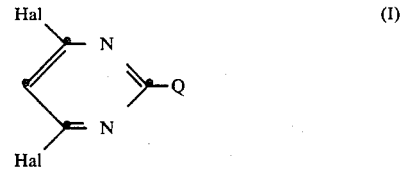

wherein Hal is a halogen atom and Q is a substituted phenyl or naphthyl radical or a heterocyclic ring which is unsaturated, partly saturated and/or fused to a benzene ring, are able to protect cultivated plants from the phytotoxic action of herbicides. The cultivated plants are preferably sorghum, cereals, maize, rice and soybeans, and the herbicides are chloroacetanilides or other compounds having herbicidal action.

4 Claims, No Drawings

2-PHENYLPYRIMIDINES, 2-NAPHTHYLPYRIMIDINES AND 2-HETEROCYCLYLPYRIMIDINES AS SAFENERS FOR PROTECTING CULTIVATED PLANT AGAINST PHYTOTOXIC DAMAGE CAUSED BY HERBICIDES

This application is a continuation, of application Ser. No. 499,603, filed May 31, 1983 now abandoned.

The present invention relates to 2-phenylpyrimidines, 2-naphthylpyrimidines and 2-heterocyclylpyrimidines which are suitable for use as safeners for protecting cultivated plants against phytotoxic damage caused by herbicides. The pyrimidines of this invention are applied to the crops of cultivated plants simultaneously with the herbicide or shortly afterwards. It is also possible to apply a composition which contains both the herbicide and the pyrimidine or to pretreat the seeds of the cultivated plants with the pyrimidine (seed dressing) and subsequently to apply the herbicide pre- or post-emergence to the crop area. The invention also relates to compositions which contain the compounds of the invention and to a method of use thereof.

It is known that herbicides belonging to a very wide range of compound classes such as triazines, urea derivatives, carbamates, thiocarbamates, haloacetanilides, halophenoxyacetic acids etc., when employed in an effective concentration, often also damage cultivated plants to a certain extent in addition to the weeds which it is desired to control. Too high concentrations are often applied unintentionally and randomly whenever peripheral zones overlap on zonal spraying, whether as a consequence of the action of wind or through miscalculating the sweep of the spray device employed. The climatic conditions or the nature of the soil may be such that the concentration of herbicide recommended for normal conditions acts as an overdose. The quality of the seeds may also be a factor in the tolerance of the herbicide. To counteract this problem, different compounds have already been proposed which are able specifically to antagonise the harmful action of the herbicide on the cultivated plant, i.e. to protect the cultivated plant without noticeably influencing the herbicidal action on the weeds to be controlled. However, it has been found that the proposed safeners very often have a species-specific activity both with respect to the cultivated plants and to the herbicide and also, in some cases, contingent on the mode of application, i.e. a specific safener is often suitable only for a specific cultivated plant and a few classes of herbicides.

The 2-phenylpyrimidines, 2-naphthylpyrimidines and 2-heterocyclylpyrimidines of the present invention have the formula I

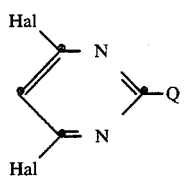 (I)

wherein Hal is halogen atom, Q is a phenyl radical

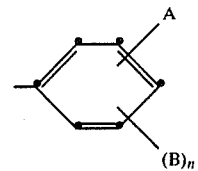

a naphthyl radical or a heterocyclic ring which is unsaturated, partly saturated or also fused to a benzene ring.

In particular, Q is a phenyl radical which is substituted by A and $(B)_n$, a 1- or 2-naphthyl radical or a heterocyclic ring which is unsaturated, partly saturated or also fused to a benzene ring, and which is unsubstituted or substituted by one or more identical or different members selected from halogen, nitro, cyano, $XR_3$, $COR_3$, $COOR_3$, $CONR_3R_4$, $NR_3R_4$, $SO_3H$ or $SO_2NR_3R_4$, or by a $C_1$–$C_6$alkyl group which is in turn unsubstituted or substituted by halogen, nitro, cyano or an $XR_3$ or $NR_3R_4$ group, or by a $C_2$–$C_6$alkenyl group which is in turn unsubstituted or substituted by halogen, cyano or an $XR_3$ group, or by a $C_2$–$C_6$alkynyl group. In these groups, the various symbols are defined as follows:

A is a radical $R_1$, $XR_1$, $COR_1$ or $XCOR_1$, $C_1$–$C_6$alkyl substituted by $R_1$ or $XR_1$, $C_2$–$C_6$alkenyl substituted by cyano, $R_1$, $XR_1$, $COR_1$ or $COR_2$, or is $C_2$–$C_6$alkynyl substituted by $R_1$ or $XR_1$, or is a radical —O—$CONR_8R_9$, —$OSO_2R_9$ or —$NR_3$—$SO_2R_9$, X is oxygen, sulfur, or the —SO— or —$SO_2$— group, $R_1$ is a phenyl radical or an unsaturated heterocyclic radical which is unsubstituted or substituted by halogen, $C_1$–$C_4$alkyl, $C_1$–$C_4$haloalkyl, nitro, cyano or X—$C_1$–$C_4$alkyl, $R_2$ is hydrogen, $C_1$–$C_6$alkyl which is unsubstituted or substituted by hydroxyl, $C_1$–$C_6$alkoxy, —$COR_2$, —$NR_3R_4$, or is $C_2$–$C_6$alkenyl or $C_2$–$C_6$alkynyl, $R_3$ and $R_4$, each independently of the other, is hydrogen, $C_1$–$C_6$alkyl which is unsubstituted or unsubstituted by hydroxyl, $C_1$–$C_6$alkoxy, —$COR_2$ or —$NR_3R_4$, or is $C_2$–$C_6$alkenyl or $C_2$–$C_6$alkynyl; or $R_3$ and $R_4$ together form a 4- to 6-membered alkylene chain which may be interrupted in the chain of atoms by oxygen, sulfur, the imino group or a $C_1$–$C_4$alkylimino group; and A is also a radical $SO_2NR_3R_4$, —N=$CR_1R_5$ or

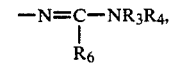

wherein $R_5$ is hydrogen, $C_1$–$C_6$alkyl which is unsubstituted or substituted by X—$C_1$–$C_6$alkyl, $R_6$ is hydrogen or $C_1$–$C_6$alkyl, or is a pyrryl, piperozyl, imidazolyl or triazolyl radical which is bound through nitrogen and is unsubstituted or substituted by $C_1$–$C_4$alkyl or halogen, or is a radical —$NR_3R_7$, wherein $R_7$ is a $R_1$, $COR_1$, $XCOR_1$, $C_1$–$C_6$alkyl or $C_3$–$C_6$cycloalkyl group, each substituted by halogen, hydroxyl, $C_1$–$C_6$alkoxy, $C_1$–$C_6$alkylthio, —$NR_3R_4$ or $R_1$, or $R_3$ and $R_7$ together form a 4- to 6-membered alkylene chain which may be interrupted in the chain of atoms by oxygen, sulfur, the imino group or a $C_1$–$C_4$alkylimino group, $R_8$ is hydrogen, $C_1-C_6$alkyl, $C_3-C_6$alkenyl, $C_3-C_6$alkynyl, $C_1-C_6$alkoxy, $C_3-C_6$alkenyloxy or $C_3-C_6$alkynyloxy, $R_9$ has the same meaning as $R_1$ or is $C_1-C_4$alkyl, $C_1-C_6$haloalkyl, $C_3-C_6$alkenyl or $C_3-C_6$alkynyl, B is hydrogen, nitro, halogen, cyano, an $XR_2$, $NR_3R_4$, $C_1-C_6$alkyl or $C_3-C_6$cycloalkyl group, each unsubstituted or substituted by halogen or $XR_2$, or is $C_2-C_6$alkenyl or $C_2-C_6$alkynyl; or A and B together form a 3- or 4-membered chain, the members of which are formed by oxygen, sulfur, a —$CH_2$—, —CH=, —NH—, —N($C_1-C_4$alkyl)—, CH—$C_1-C_4$alkyl—, —C($C_1-C_4$)alkyl=, C($C_1-C_4$alkyl)$_2$— or —CO— group, with the proviso that two oxygen and/or sulfur atoms are not directly adjacent ring members, n is 0 or 1, and Hal is halogen.

Alkyl by itself or as moiety of another substituent comprises branched or unbranched alkyl groups which contain the indicated number of carbon atoms. Examples of such alkyl groups are: methyl, ethyl, propyl, isopropyl, butyl, isobutyl, sec-butyl, tert-butyl, as well as the higher homologs amyl, isoamyl, hexyl, heptyl, octyl, together with their isomers. The alkenyl and alkynyl groups can likewise be straight chain or branched. Cycloalkyl groups are cyclopropyl, cyclobutyl, cyclopentyl and cyclohexyl. The alkenyl and alkynyl radicals may be branched or unbranched and contain one or more double or triple bonds.

Unsaturated, partly saturated and/or fused 5- or 6-membered heterocyclic rings falling within the definition of Q are e.g. furan, pyran, thiophene, thiazole, pyridine, pyrroline, oxazole, isoxazole, thioxazole, isothiazole, thiadiazole, oxthiazole, pyrrole, imidazole, pyrazole, pyrazine, pyrimidine, pyridazine, 1,3,5-triazine, 1,2,4-triazine, 1,2,4-triazole, 1,2,3-triazole, 1,3,4-triazole, oxdiazole, oxazine, furazane, pyridine-N-oxide, thiophene-5-oxide, benzthiophene, benzofurane, pyridine-N-oxide, thiophene-5-oxide, benzthiophene, benzofuran, isobenzofuran, chromene, chroman, indole, isoindole, indazole, quinoline, isoquinoline, phthalazine, quinoxaline, quinazoline, cinnoline, benzthiazole, benzimidazole.

These rings are attached to the pyrimidine ring through a carbon atom or, in the case of N-heterocycles, also through a nitrogen atom. They may be unsubstituted or substituted as indicated above.

The phenylpyrimidines of the formula I are most suitable for protecting cultivated plants such as sorghum, rice, maize, cereals (wheat, rye, barley, oats), cotton, sugar beet, sugar cane, soybeans etc., from attack by aggressive agrochemicals, especially by herbicides belonging to a wide variety of compound classes, e.g. triazines, phenylurea derivatives, carbamates, thiocarbamates, haloacetanilides, halophenoxyacetates, substituted phenoxyphenoxyacetates and -propionates, substituted pyridyloxyphenoxyacetates and -propionates, benzoic acid derivatives etc., where these compound do not have a selective action or do not act selectively enough, i.e. where they also damage the cultivated plants to a greater or lesser extent in addition to the weeds which it is desired to control. The invention also relates to compositions which contain these phenylpyrimidines of the formula I together with herbicides.

Useful compounds of the formula I are those comprised by the following subgroups:

Phenylpyrimidines of the formula Ia

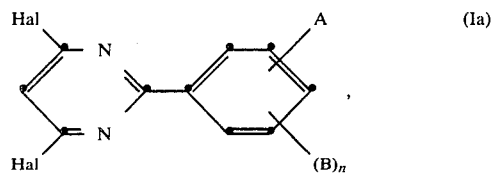

wherein Hal, A, B, and n are as defined above, in particular those wherein:

(a) A is a radical $R_1$ or $XR_1$, and B, Hal, n, $R_1$ and X have the meanings assigned to them above;

(b) A is $C_1-C_6$alkyl substituted by $R_1$ or $XR_2$, $C_2-C_6$alkenyl substituted by cyano, $R_1$, $XR_1$, $COR_1$ or $COR_3$, or $C_1-C_6$alkynyl substituted by $R_1$ or $XR_1$, and B, Hal, n, $R_1$ and $R_3$ have the meanings assigned to them above;

(c) A is a radical $NR_3R_7$, and B, Hal, n, $R_3$, $R_7$ and X are as defined above;

(d) A and B together form a 3- or 4-membered chain, the members of which are formed by oxygen, sulfur, —$CH_2$—, —CH=, —CH($C_1-C_4$alkyl)—, —C($C_1-C_4$alkyl)=, —C($C_1-C_4$alkyl)$_2$— or —CO—, with the proviso that two oxygen and/or sulfur atoms are not adjacent ring members, n is 1 and Hal is a halogen atom;

(e) A is a pyrrolyl, pyrazolyl, piperazolyl, imidazolyl or triazolyl radical which is bound through oxygen and is unsubstituted or substituted by $C_1-C_4$alkyl or halogen, and B, Hal and n are as defined above.

The 2-naphthylpyrimidines of the formula I, wherein Hal denotes halogen atoms, especially chlorine or bromine atoms, are very effective.

Good protection is also obtained with the compounds of formula I, wherein Q is a 5- or 6-membered heterocyclic radical which is unsaturated, partly saturated and/or fused to a benzene ring, and which is unsubstituted or substituted as indicated above.

The best protection is obtained with those compounds of formula I, wherein Q is an unsubstituted or substituted naphthyl, furyl, thienyl or pyridyl radical, in particular also the following compounds:

4,6-dichloro-2-(2'-furyl)pyrimidine,
4,6-dichloro-2-(2'-thienyl)pyrimidine,
4,6-dichloro-2-(3'-thienyl)pyrimidine,
4,6-dichloro-2-(1'-naphthyl)pyrimidine,
4,6-dichloro-2-(2'-pyridyl)pyrimidine,
4,6-dichloro-2-(3'-pyridyl)pyrimidine,
4,6-dichloro-2-(4'-pyridyl)pyrimidine,
4,6-dichloro-2-(5'-bromopyrid-3'-yl)pyrimidine,
4,6-dichloro-2-(3'-pyridyl-N-oxide)pyrimidine,
4,6-dichloro-2-(4',6'-dimethylpyrimidin-2'-yl)pyrimidine,
4,6-dichloro-2-(3'-quinolyl)pyrimidine,
4,6-dichloro-2-(2'-methylthien-5'-yl)pyrimidine,
4,5-dichloro-2-(2'-pyrrolyl)pyrimidine,
4,6-dichloro-2-(1'-methylpyrrol-2'-yl)pyrimidine,
2-(3,4-methylendioxyphenyl)-4,6-dichloropyrimidine,
2-(4-benzylideniminophenyl)-4,6-dichloropyrimidine,
2-(4-N-benzylaminophenyl)-4,6-dichloropyrimidine,
2-(4-dihydroxyethylaminophenyl)-4,6-dichloropyrimidine,
2-8 4-(2-cyano-2'-carboxylethenyl)phenyl]-4,6-dichloropyrimidine,
2-(4-styrylphenyl)-4,6-dichloropyrimidine, 2-(4-N-methoxy-N-methylcarbamoylphenyl)-4,6-dichloropyrimidine,
2-(4-N-phenylcarbamoyloxyphenyl)-4,6-dichloropyrimidine,
2-(3-N-methylcarbamoyloxyphenyl)-4,6-dichloropyrimidine,
2-(3-dimethylaminomethyleniminophenyl)-4,6-dichloropyrimidine,
2-(4-N-methoxy-N-methylcarbamoyloxyphenyl)-4,6-dichloropyrimidine,
2-(4-phenylethynylphenyl)-4,6-dichloropyrimidine,
2-p-diphenyl-4,6-dichloropyrimidine,
2-(4-pyrimidin-2-ylphenyl)-4,6-dichloropyrimidine,
2-p-diphenylether-4,6-dichloropyrimidine,
2-(4-p-chlorophenoxyphenyl)-4,6-dichloropyrimidine,
2-[4-(1,1-dimethylaminomethylidenimino)phenyl]-4,6-dichloropyrimidine,
2-[3-(1,1-dimethylaminomethylidenimino)phenyl]-4,6-dichloropyrimidine,
2-(4-pyrrolylphenyl)-4,6-dichloropyrimidine,
2-(3-pyrrolylphenyl)-4,6-dichloropyrimidine,
2-indan-4-yl-4,6-dichloropyrimidine,
2-(4-hydroxypropylaminophenyl)-4,6-dichloropyrimidine,
2-(4-dihydroxypropylaminophenyl)-4,6-dichloropyrimidine,
2-(4-phenoxy-n-propoxyphenyl)-4,6-dichloropyrimidine.

Various compounds which are able to antagonise specifically the harmful effects of a herbicide on cultivated plants have already been proposed as safeners or antidotes, i.e. compounds which protect cultivated plants without noticeably influencing the herbicidal action on the weeds which it is desired to control. Depending on their properties, such antidotes, also known as safeners, can be used for pretreating the seeds of the cultivated plants (dressing seeds or seedlings) or before sowing seeds in furrows, or as tank mixture together with the herbicide pre- or postemergence.

For example, British patent specification No. 1 277 557 discloses the treatment of seed and seedlings of wheat and sorghum with certain esters and amides of oxamic acid to protect them from attack by N-methoxymethyl-2′,6′-diethyl-chloroacetanilide (Alachlor). Other publications (German Offenlegungsschrift specifications Nos. 1 952 910 and 2 245 471, and French patent specification No. 2 021 611), propose antidotes for the treatment of cereals, maize seeds and rice seeds to protect them from attack by thiocarbamate herbicides. in German patent specification No. 1 576 676 and U.S. patent specification No. 3 131 509, hydroxyaminoacetanilides and hydantoins are suggested for protecting cereal seeds against carbamates such as IPC, CIPC, etc. Further development, however, has shown all these preparations to be unsatisfactory.

Surprisingly, phenylpyrimidines of the formula I have the property of protecting cultivated plants from attack by aggressive agrochemicals, in particular from herbicides belonging to a wide range of compound classes, for example chloroacetanilides, chloroacetamides, carbamates and thiocarbamates, diphenyl ethers and nitrodiphenyl ethers, benzoic acid derivatives, triazines and triazinones, phenylureas, nitroanilines, oxdiazolones, pyridyloxyphenoxy derivatives, phosphates and pyrazoles, where these compounds are not tolerated or are insufficiently tolerated by the cultivated plants.

The phenylpyrimidines of this invention preferably protect cultivated plants from attack by herbicides belonging to the classes of the chloroacetanilides, chdloroacetamides, thiocarbamates, and phosphates.

Depending on the end use, the safener or antidote of the formula I can be used for pretreating seeds of the cultivated plant (dressing of the seeds or seedlings) or it can be added to the soil before or after sowing. However, it can also be applied pre- or post-emergence by itself alone or together with the herbicide. The treatment of the plant or seeds with the safener can therefore in principle be carried out independently of the time of application of the phytotoxic chemical. It can, however, also be carried out by simultaneous application of phytoxic chemical and safener (tank mixture). The preemergence treatment includes both treatment of the crop area before sowing (ppi=pre-plant incorporation) and treatment of the crop areas after sowing but before emergence of the plants.

The rates of application of the safener with respect to the herbicide depend largely on the mode of application. Where a field treatment is carried out, either simultaneously as tank mixture or with separate application of herbicide and antidote, the ratio of safener to herbicide is in the range from 1:100 to 10:1, with the preferred range being from 1:5 to 8:1, most preferably however 1:1. When dressing seeds and taking similar specific protective measures, however, much lower amounts of antidote are required compared with e.g. the amounts of herbicide later employed per hectare of crop area. For seed dressing, 0.1 to 10 g of antidote per kg of seeds are required, with the preferred amount being from 1 to 2 grams. If it is desired to apply the safener shortly before sowing by seed pretreatment, safener solutions which contain the active ingredient in a concentration of 1 to 10,000 ppm, preferably of 100 to 1000 ppm, are used.

As a rule there is a substantial interval of time between protective measures such as seed dressing and treatment of seedlings with a safener of the formula I and the possible later field treatment with agricultural chemicals. Pretreated seeds and plants can later come in contact with different chemicals in agriculture, horticulture and forestry. Accordingly, the invention relates to plant protection compositions which contain a safener of the formula I as active ingredient, together with conventional carriers. If appropriate, such compositions may be additionally mixed with the chemical against whose effects it is desired to protect the cultivated plant, e.g. with a herbicide.

Cultivated plants within the scope of this invention are all plants which, in any form, can be harvested (seeds, roots, stalks, tubers, leaves, blossoms) and from which extracts can be obtained (oils, sugar, stearch, protein) and which are cultivated for this purpose.

These plants comprise e.g. all species of cereals such as wheat, rye, barley, oats and, in particular, rice, sorghum, maize, and also cotton, sugar beet, sugar cane, soybeans, beans, and peas.

The antidote can be employed wherever it is desired to protect a cultivated plant of the kind indicated above from the harmful effects of an agricultural chemical. Examples of herbicides whose action it is desired to protect the cultivated plants are the following compounds:

Chloroacetanilides: 2-chloro-2′,6′-diethyl-N-(2″-propoxyethyl)acetanilide ("propalochlor"), 2-chloro-6′-ethyl-N-(2″-methoxy-1″-methylethyl)acet-o-toluidide ("metolachlor"), 2-chloro-2',6'-diethyl-N-(butoxymethyl)acetanilide ("butachlor"), 2-chloro-6'-ethyl-N-(ethoxymethyl)acet-o-toluidide ("acetochlor"), 2-chloro-6'-ethyl-N-(2"-propoxy-1"-methylethyl)acet-o-toluidide, 2-chloro-2',6'-dimethyl-N-(2-methoxy-1"-methylethyl)acetanilide, 2-chloro-2',6'-dimethyl-N-(2"-methoxyethyl)acetanilide ("dimethachlor"), 2-chloro-2',6'-diethyl-N-(pyrazol-1-ylmethyl)acetanilide, 2-chloro-6'-ethyl-N-(pyrazol-1-ylmethyl)aceto-toluidide, 2-chloro-6'-ethyl-N-(2"-butoxy-1"-methylethyl)acet-o-toluidide ("metazochlor"), 2-chloro-6'-ethyl-N-(2"-butoxyl-1"-(methylethyl)-acet-o-toluidide, 2-chloro-2'-trimethylsilyl-N-(butoxymethyl)acetanilide, 2-chloro-2',6'-diethyl-N-(methoxymethyl)acetanilide("alachlor"), 2-chloro-2',6'-diethyl-N-(ethoxycarbonylmethyl)acetanilide, 2-chloro-2',6'-dimethyl-N-(2"-n-propoxyethyl)acetanilide, 2-chloro-2',6'-ethyl-6'-methyl-N-(2"-n-propoxyethyl)acetanilide, 2-chloro-2',6'-dimethyl-N-(isobutoxymethyl)acetanilide, 2-chloro-2',6'-dimethyl-N-(isopropoxymethyl)-acetanilide or 2-chloro-2',6'-tert-butyl-N-(butoxymethyl)acetanilide ("terbuchlor").

Chloroacetamides: N-[1-isopropyl-2-methylpropen-1-yl(1)]-N-(2'-methoxyethyl)-chloroacetamide, N-(2'-butoxyethyl)-N-(2,6-dimethyl-1-cyclohexen-1-yl)-chloroacetamide and N-isopropyl-2-chloro-N-(3,3,5-trimethyl-1-cyclohexen-1-yl)-chloroacetamide.

Dimedones: 2-[1-(ethoximino)butyl]-5-(ethylthio)propyl-3-hydroxy-2-cyclohexen-1-one ("sethoxydin") and the sodium salt of 2-[1-(N-allyloxamino)-butylidene]-5,5-dimethyl-4-methoxycarbonyl-cyclohexane-1,3-dione ("alloxdimedon").

Carbamates and thiocarbamates: N-(3',4'-dichlorophenyl)-propionanilide ("propanil"), S-4-chlorobenzyl-diethylthiocarbamate ("benthiocarb"), S-ethyl-N,N-hexamethylenethiocarbamate ("molinate"), S-ethyl-dipropylthiocarbamate ("EPTC"), N,N-di-sec-butyl-S-benzyl-thiocarbamate (drepamon), S-(2,3-dichloroallyl)-diisopropylthiocarbamate ("diallate"), S-(2,3,3-trichloroallyl)-diisopropylthiocarbamate ("triallate"), 1-(propylthiocarbonyl)-decahydroquinaldine, S-4-benzyldiethylthiocarbamate and corresponding sulfinylcarbamates.

Diphenyl ethers and nitrodiphenyl ethers: 2,4-dichlorophenyl-4'-nitrophenyl ether ("nitrofen"), 2-chloro-1-(3'-ethoxy-4'-nitrophenoxy)-4-trifuloromethylbenzene ("oxyfluorfen"), 2',4'-dichlorophenyl-3-methoxy-4-nitrophenyl ether ("chlormethoxynil"), methyl 2-[4'-(2",4"-dichlorophenoxy)phenoxy]propionate ("hoelon"), N-(2'-methoxyethyl)-2-[5'(2"-chloro-4"-trifluoromethylphenoxy)-phenoxy]propionic acid, butyl α-[4-(4-trifluoromethylphenoxy)-phenoxy]propionate ("fluazifopbutyl").

Benzoic acid derivatives: methyl-5-(2',4'-dichlorophenoxy)-2-nitrobenzoate ("bifenox"), 5-(2'-chloro-4'-trifluoromethylphenoxy)-2-nitrobenzoic acid ("acifluorfen"), 2,6-dichlorobenzonitrile ("dichlobenil").

Triazines and triazinones: 2,4-bis(isopropylamino)-6-methylthio-1,3,5-triazine ("prometryn"), 2,4-bis(ethylamino)-6-methylthio-1,3,5-triazine ("symetryn"), 2-(1',2'-dimethylpropylamino)-4-ethylamino-6-methylthio-1,3,5-triazine ("dimethametryn"), 4-amino-6-tert-butyl-4,5-dihydro-3-methylthio-1,2,4-triazin-5-one ("metribuzin").

Phenylureas: N'-(3'-isopropylphenyl)-N',N'-dimethylurea ("isoproturon"), N-(3',4'-dimethylbenzyl)-N-4-tolylurea ("dimuron"), N-(3'-chloro-4'isopropylphenyl)-N',N'-(3-methylpentamethylen-1,5-yl)urea.

Nitroanilines: 2,6-dinitro-N,N-dipropyl-4-trifluoromethylaniline ("trifluralin"), N(1'-ethylpropyl)-2,6-dinitro-3,4-xylidine ("pendimethalin").

Oxadiazolones: 5-tert-butyl-3(2',4'-dichloro-5'-isopropoxyphenyl)-1,3,4-oxadiazol-2-one ("oxadiazon").

Pyridyloxyphenoxy derivatives: propynyl 2-[4'-(3",5"-dichloropyridyl2"-oxy)phenoxy]propionate ("chloazifop-propynyl").

Phosphates: S-2-methylpiperidinocarbonylmethyl-0,0-dipropylphosphorodithioate ("piperophos"), S-(N-isopropyl-4-chloroanilido)carbonylmethyl-CO-dimethyldithionate ("anilophos").

Pyrazoles: 1,3-dimethyl-4-(2',4'-dichlorobenzoyl)-5-(4'-tolylsulfonyloxy)pyrazole.

Miscelleaneous: 2-ethoxy-2,3-dihydro-3,3-dimethylbenzofuran-b 5-ylmethanesulfonate ("ethofumesat").

The 2-phenyl-, 2-naphthyl- or 2-heterocyclylpyrimidine of the formula I, or the composition containing this safener, may be applied before or after the application of the herbicide or simultaneously with it. Treating the seeds by a solution containing the safener (seed dressing) has proved to be a particularly efficient method of treatment. The solvent can be evaporated off and the seeds, coated with a layer of safener, then sown; or the seeds can be soaked in an aqueous solution containing the safener and sown in this condition, as is usually done e.g. with rice.

The 2-phenyl-, 2-naphthyl- and 2-heterocyclylpyrimidines of the formula I may be prepared by reacting a naphthylcyanide or heterocyclic cyanide of the formula II $$Q-CN \qquad (II)$$

with sodium methylate in methanol, to give the methoxyimine of the formula III $$Q-\underset{NH}{\overset{\|}{C}}-OCH_3 \qquad (III)$$

and further with ammonia or an ammonium salt to give the amidine of the formula IV $$Q-\underset{NH}{\overset{\|}{C}}-NH_2 \qquad (IV)$$

and subsequently condensing this latter with a dialkyl malonate to give the 2-phenyl-, 2-naphthyl- or 2-heterocyclylpyrimidine of the formula V which is then reacted with a halogenating agent, to give the 2-phenyl-, 2-naphthyl- or 2-heterocyclylpyrimidine of the formula I. Q in the above formulae is as defined in formula I. These reactions take place for the most part at room temperature in organic polar solvents. Where a sodium alcoholate is used, the solvent will be the corresponding alkanol; otherwise, suitable solvents are ketones, ethers or aromatic hydrocarbons. The condensation of the amidine with the malonate is preferably carried out at the boiling temperature of the reaction mixture.

In another preparatory method, the cyanide of formula II can be converted with sodium amide, in an aromatic hydrocarbon as solvent, direct to the amidine of the formula IV, which is then condensed with dialkyl malonate.

In a further process, the cyanide of the formula II may be converted with hydrogen chloride gas and an alcohol, in an inert solvent, to the hydrochloride of the methoxyimine of the formula III, and by further treatment with methanolic ammonia to the hydrochloride of the amldine of the formula IV.

The process for the preparation of the 2-naphthyl- or 2-heterocyclylpyrimidines of the formula I comprises reacting a 4,6-dihydroxy-2-naphthyl- or -2-heterocyclylpyrimidine of the formula V

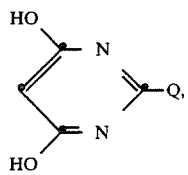
(V)

wherein Q is as defined for formula I, with halogen or a halogen donor, in an inert organic solvent, and isolating the 4,6-dihalo-2-phenyl-, -2-naphthyl- or -2-heterocyclylpyrimidine of the formula I so obtained, and, if desired, reacting said pyrimidine with an equimolar amount of sodium salt in an inert organic solvent.

These reactions are carried out in the temperature range from $-20°$ C. to the boiling point of the solvent, preferably at room temperature. Suitable solvents are alkanols, ketones, ethers, aromatic hydrocarbons and also e.g. dimethylsulfoxide.

The 2-phenylpyrimidines of the formula I may be used by themselves alone or together with the herbicides which it is desired to antagonise.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphahtic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g., the sodium or potassium salts of oleic or stearic acid, or of natural fatty acid mixtures which can be obtained e.g. from coconut oil or tallow oil. Mention may also be made of fatty acid methyltaurin salts.

More frequently, however, so called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthylenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples on non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$-$C_{22}$ alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ringwood, N.J., 1979, and Sisely and Wood, "Encyclopedia of Surface Active Agents", Chemical Publishing Co., Ing. New York, 1964.

These compositions usually contain 0.1 to 99%, preferably 0.1 to 95%, of a compound of the formula I, 1 to 99% of a solid or liquid adjuvant, and 0 to 25%, preferably 0.1 to 25%, or a sur factant.

Whereas commercial products are preferably formulated as concentrates, the end user will normally employ dilute formulations.

The compositions may also contain further ingredients, such as stabilisers, antifoams, viscosity regulators, binders, tackifiers as well as fertilisers or other active ingredients in order to obtain special effects.

The invention is illustrated in more detail by the following Examples, without implying any restriction to what is described therein. Parts and percentages are by weight.

EXAMPLE 1

Preparation of 2-(3,4-methylenedioxyphenyl)-4,6-dichloropyrimidine

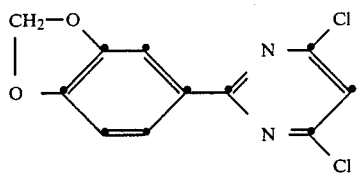

(Compound 256)

A mixture of 7 g of 2-(3,4-methylenedioxyphenyl)-4,6-dihydroxypyrimidine, 6 ml of phosphorus trichloride, 7,6 ml of N,N-dimethylaniline and 30 ml of toluene is refluxed for 3 hours. The soluton is finally concentrated and the residue is taken up in methylene chloride. The methylene chloride solution is clarified with fuller's earth, dried over magnesium sulfate and crystallised, affording 6.3 g of the title compound with a melting point of 148°-150° C.

The starting 2-(3,4-methylenedioxyphenyl)-4,6-dihydroxypyrimidine is obtained as follows:

A solution of 25 g of 3,4-methylenedioxybenzonitrile in 10 ml of methanol and 170 ml of ethylene chloride is saturated at 0°-5° C. with hydrogen chloride gas. The solution is stirred overnight at room temperature and then excess hydrogen chloride is expelled with nitrogen. Then 50 ml of a solution of 10N ammonia in methanol are added and the batch is refluxed for 2 hours and finally concentrated by rotary evaporation. The residue is dissolved in 140 ml of methanol, then 26 ml of diethyl malonate and 92 ml of 30% sodium methylate are added and the mixture is refluxed for 6 hours. The methanol is evaporated off and the residue is dissolved in 700 ml of water. The aqueous solution is filtered and acidified with concentrated hydrochlorid acid (pH 1). The precipitate is isolated by filtration, washed with water and dried, affording 34.6 of 2-(3,4-methylenedioxyphenyl)-4,6-dihydroxypyrimidine which melts only above 300° C.

EXAMPLE 2

Preparation of 2-(4-benzylidene-iminophenyl)-4,6-dichloropyrimidine

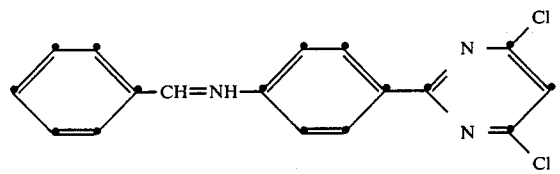

(compound 206)

A solution of 12 g of 2-(4-aminophenyl)-4,6-dichloropyrimidine, 6 g of benzaldehyde and 100 mg of p-toluenesulfonic acid are boiled for 4 hours in 100 ml of toluene using a water separator. The reaction solution is then concentrated to half its volume and then 50 ml of hexane are added. Crystals of 2-(4-benzylidene-iminophenyl)-4,6-dichloropyrimidine precipitate from the cooled solution. Yield: 10.5 g. The product decomposes at 190° C.

EXAMPLE 3

Preparation of 2-(4-benzoylamidophenyl)-4,6-dichloropyrimidine

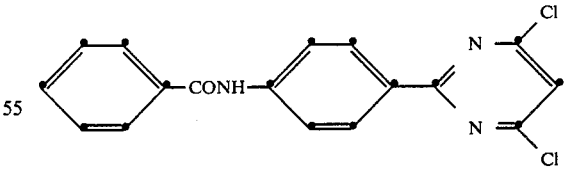

(compound 261)

With stirring, 3.5 g of benzoyl chloride are added dropwise to a solution of 6 g of 2-(4-aminophenyl)-4,6-dichloropyrimidine, 3 g of triethylamine and 200 mg of 4-dimethylaminopyridine in 100 ml of tetrahydrofuran. When the addition is complete, the reaction mixture is stirred overnight at room temperature. The solution is then poured into water and the precipitate is isolated, washed and dried, affording 8.8 g of 2-(4-benzoylamidophenyl)-4,6-dichloropyrimidine with a melting point of 198°-200° C.

EXAMPLE 4

Preparation of 2-[4-(2',2'-dihydroxyethylamino)phenyl]-4,6-dichloropyrimidine

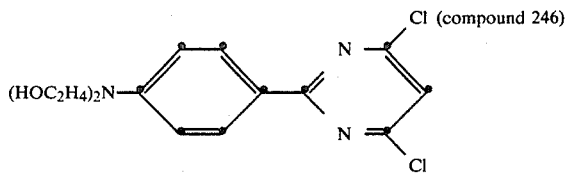
(compound 246)

With stirring, 48 g of 2-(4-aminophenyl)-4,6-dichloropyrimidine and 0.5 ml of boron trifluoride etherate are added, in portions, at 0° C. to a solution of 12.5 g of ethylene oxide in 300 ml of toluene. The suspension is stirred for 30 minutes at 5°–10° C., for 1 hour at room temperature, and finally for 1 hour at 60° C. The product is then isolated by filtration, washed with toluene and dried affording 33 g of title compound with is recrystallised from tetrahydrofuran/hexan and melts at 169°–171° C.

EXAMPLE 5

Preparation of 2-[4-(2'-carboxy-2'-cyanoethyl)phenyl]-4,6-dichloropyrimidine

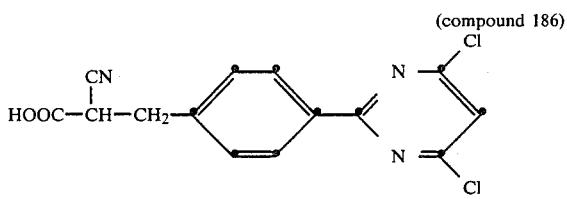
(compound 186)

A solution of 12.5 g of 2-(4-formylphenyl)-4,6-dichloropyrimidine, 45 g of cyanoacetic acid, 0.2 ml of acetic acid and 0.05 ml of pyrrolidine in 150 ml of toluene is boiled for 1 hour using a water separator. A small amount of toluene is then distilled off and the solution is cooled, affording 15.9 g of crystalline 2-[4-(2'-cyano-2-carboxyethenyl)phenyl]-4,6-dichloropyrimidine which melts at 240° C.

EXAMPLE 6

Preparation of 4,6-dichloro-2-(2'-furyl)pyrimidine

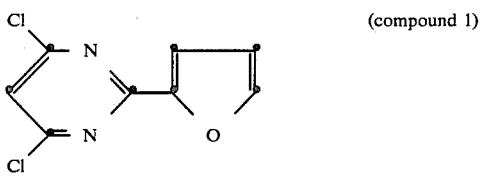
(compound 1)

A mixture of 10 g of 4,6-dihydroxy-2-(2'-furyl)pyrimidine, 10 ml of N,N-dimethylaniline and 50 ml of phosphorus trichloride is refluxed for 3 hours. The reaction solution is then concentrated in vacuo in a rotary evaporator and the residue is poured into ice/water. The aqueous solution is extracted repeatedly with ethyl acetate and the organic phases are washed, clarified with fuller's earth, dried and concentrated. The residue is recrystallised from ether/hexane, affording 6.5 g of the title compound with a melting point of 70°–72° C.

The starting 4,6-dihydroxy-2-(2'-furyl)pyrimidine is prepared as follows:

A solution of 25 g of 2-cyanofuran and 0.5 ml of 30% sodium methylate in 75 ml of methanol is prepared and stirred for 4 hours at 20° C. Then 16 g of ammonium chloride are added and the mixture is stirred at room temperature overnight. Then 43 of diethyl malonate and 108 ml of 30% sodium methylate in MeOH are added and the batch is refluxed for 5 hours. The reaction mixture is then cooled, poured into 500 ml of ice/water and acidified with concentrated hydrochloride acid to pH 2. The precipitate is isolated by filtration, washed with water and dried in vacuo at 100° C., affording 36 g of 4,6-dihydroxy-2-(2'-furyl)pyrimidine which melts at above 315° C. with decomposition.

EXAMPLE 7

Preparation of 4,6-dichloro-2-(3-thienyl)pyrimidine

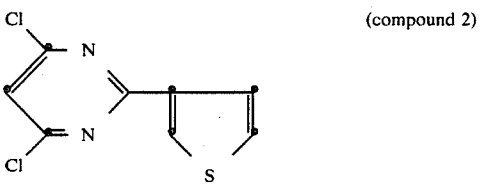
(compound 2)

A mixture of 14 g of 4,6-dihydroxy-2-(3-thienyl)pyrimidine, 10 ml of N,N-dimethylaniline and 40 ml of phosphorus trichloride is refluxed for 2 hours. The reaction solution is then concentrated in vacuo in a rotary evaporator and the residue is poured into ice/water. The aqueous solution is then extracted repeatedly with ethyl acetate and the organic phases are treated with fuller's earth, dried and concentrated. The residue is recrystallised from ether/hexane, affording 7 g of crystalline title compound with a melting point of 86°–90° C. The starting 4,6-dihydroxy-2-(3-thienyl)pyrimidine is prepared as follows:

29 g of 3-cyanothiophene are stirred in 100 ml of methanol for 20 hours at room temperature until a clear solution is obtained. To this solution are added first 3 ml of 30% sodium methylate in methanol and then, after stirring for 6 hours at room temperature, 15.5 g of ammonium chloride. Stirring is continued overnight at room temperature and then 46.4 g of diethyl malonate and 11.5 ml of sodium methylate in methanol are added and the batch is refluxed for 3½ hours. The solution is concentrated and the residue is poured into 500 ml of ice/water. The aqueous solution is acidified with concentrated hydrochloric acid to pH 2. The precipitate is isolated by filtration, washed with water and dried in vacuo at 60° C., affording 28.5 g of 4,6-dihydroxy-2-(3'-thienyl)pyrimidine with a melting point of over 300° C.

EXAMPLE 8

Preparation of 4,6-dichloro-2-(1-naphthyl)pyrimidine

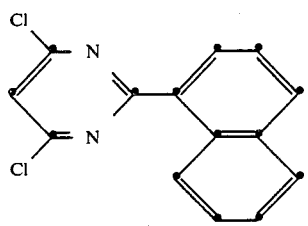

(compound 3)

A mixture of 5 g of 4,6-dihydroxy-2-(1-naphthyl)-pyrimidine, 5 ml of N,N-dimethylaniline and 20 ml of phosphorus trichloride is refluxed for 2 hours. The solution is then concentrated in vacuo in a rotary evaporator and the residue is poured into ice/water. The aqueous solution is extracted with ether, and the extracts are washed, dried, treated with fuller's earth and concentrated. The residue is recrystallised from ether/hexane, affording 3.1 g of crystalline title compound with a melting point of 111°–113° C.

The starting 4,6-dihydroxy-2-(1-naphthyl)pyrimidine is prepared as follows:

To 7.3 g of 1-naphthylcyanide in 50 ml of toluene are added, under nitrogen, 2.1 ml of 50% sodium amide in toluene and the mixture is stirred overnight at 90° C. The solution is then cooled and then 7.6 ml of diethyl malonate and 13.5 ml of 30% sodium methylate in methanol are added dropwise. When the addition is complete, the reaction mixture is cooled, diluted with 100 ml of ether, and extracted with 1N aqueous potassium hydroxide solution. The aqueous phase is acidified with concentrated HCl to pH 2 and the precipitate is isolated by filtration, washed with water and dried in vacuo at 100° C., affording 5 g of 4,6-dihydroxy-2-(1'-naphthyl)-pyrimidine with a melting point of over 300° C.

The following compounds are prepared in corresponding manner:

TABLE 1

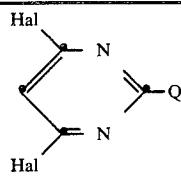

| No. | Hal | | Q | physical data (°C.) |
|---|---|---|---|---|
| 1 | Cl | Cl | 2-furyl | m.p. 70–72° (Exp. 1) |
| 2 | Cl | Cl | 3-thienyl | m.p. 86–90° (Exp. 2) |
| 3 | Cl | Cl | 1-naphthyl | m.p. 111–113° (Example 3) |
| 4 | Cl | Cl | 2-thienyl | m.p. 128–130° |
| 5 | Cl | Cl | 5-methyl-2-thienyl | m.p. 84–87° |
| 6 | Cl | Cl | 5-chloro-2-thienyl | |
| 7 | Br | Br | 2-methyl-4-thienyl | m.p. 98–100° |
| 8 | Cl | Cl | 2-methoxy-4-thienyl | |
| 9 | Br | Br | 2-thienyl | |
| 10 | Cl | Cl | 2,3-dimethyl-5-thienyl | |
| 11 | Cl | Cl | 3-methyl-2-thienyl | |
| 12 | Cl | Cl | 2-thienyl-oxyd | |
| 13 | Cl | F | 2-thienyl | |
| 14 | Cl | Cl | 2-pyrrolyl | m.p. 85–87° |
| 15 | Cl | Cl | 3-pyrrolyl | |
| 16 | Cl | Cl | 1-methyl-2-pyrrolyl | m.p. 80–82° |
| 17 | Cl | Cl | 1-methyl-3-pyrrolyl | |

TABLE 1-continued

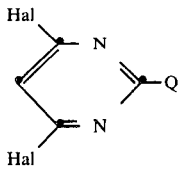

| No. | Hal | | Q | physical data (°C.) |
|---|---|---|---|---|
| 18 | Cl | Cl | 1-acetyl-3-pyrrolyl | |
| 19 | Cl | Cl | 1-pyrrolyl | m.p. 58–60° |
| 20 | Cl | Cl | 1-thinyl-3-pyrrolyl | |
| 21 | Cl | Br | 2-furyl | |
| 22 | Br | Br | 2-furyl | |
| 23 | Cl | Cl | 3-furyl | |
| 24 | Cl | Cl | 5-methoxyfuryl-(2)- | |
| 25 | Cl | Cl | 5-nitrofuryl-(2)- | |
| 26 | Cl | Cl | 5-methylfuryl-(2)- | m.p. 91–93° |
| 27 | Cl | Cl | 4-methylfuryl-(2)- | |
| 28 | Cl | Cl | 5-methoxycarbonylfuryl-(2) | |
| 29 | Cl | Cl | 5-carboxyfuryl-(2)- | |
| 30 | Cl | Cl | 3-pyrazolyl | |
| 31 | Cl | Cl | 1-methyl-4-imidazolyl | |
| 32 | Cl | Cl | 1,2,4-triazol-5-yl | |
| 33 | Cl | Cl | 1,2,3-triazol-4-yl | |
| 34 | Cl | Cl | 2-oxthien-4-yl | |
| 35 | Cl | Cl | 1,3-dithien-4-yl | |
| 36 | Cl | Cl | 1,2-dithien-4-yl | |
| 37 | Cl | Cl | 1,3-oxazol-4-yl | |
| 38 | Cl | Cl | 1,2,3-furazan-4-yl | |
| 39 | Cl | Cl | 1,2,5-furazan-3-yl | |
| 40 | Cl | Cl | 1,2,4-furazan-3-yl | |
| 41 | Cl | Cl | 1,3,4-furazan-2-yl | |
| 42 | Cl | Cl | 1,2,3,4-oxtriazol-5-yl | |
| 43 | Cl | Cl | 1,2,3,5-oxtriazol-4-yl | |
| 44 | Cl | Cl | 2,2-dihydro-1,3,4-dioxazol-5-yl | |
| 45 | Cl | Cl | 1-acetyl-3-pyrazolyl | |
| 46 | Cl | Cl | 2-allyl-1,2,4-triazol-3-yl | |
| 47 | Cl | Cl | 1-methyl-3-pyrazolyl | |
| 48 | Cl | Cl | 1,3,4-triazol-1-yl | |
| 49 | Cl | Cl | 1,2,4-triazol-4-yl | |
| 50 | Br | Br | 1,2,4-triazol-4-yl | |
| 51 | Br | Br | 1,3,4-triazol-4-yl | |
| 52 | F | Cl | 1-methyl-3-pyrazolyl | |
| 53 | Cl | Cl | 1,3-oxazol-5-yl | |
| 54 | Cl | Cl | 1,3-oxazol-4-yl | |
| 55 | Cl | Cl | 1,3-oxazol-2-yl | |
| 56 | Br | Br | 1,3-oxazol-2-yl | |
| 57 | Cl | Cl | 1,2-oxazol-3-yl | |
| 58 | Cl | Cl | 1,3-thiazol-4-yl | |
| 59 | Cl | Cl | 1,3-thiazol-5-yl | |
| 60 | Br | Br | 1,3-thiazol-2-yl | |
| 61 | Cl | Cl | 1,3-thiazol-2-yl | |
| 62 | Cl | Cl | 2-methyl-1,3-thiazol-5-yl | m.p. 108–110° |
| 63 | Cl | Cl | 2-isopropyl-1,3-thiazol-4-yl | |
| 64 | Cl | Cl | 1,2-thiazol-5-yl | |
| 65 | Cl | Cl | 4-carbomethoxy-1,3-thiazol-2-yl | |
| 66 | Cl | Cl | 2-pyridyl | m.p. 175–178° |
| 67 | Br | Br | 2-pyridyl | |
| 68 | Cl | F | 2-pyridyl | |
| 69 | Cl | Cl | 3-pyridyl | m.p. 117–120° |
| 70 | Br | Br | 3-pyridyl | |
| 71 | Cl | Cl | 4-pyridyl | m.p. 150–152° |
| 72 | Cl | Cl | 4-pyridyl-N—oxide | m.p. 192° |
| 73 | Br | Br | 4-pyridyl | |
| 74 | Cl | Cl | 5-bromopyrid-3-yl | m.p. 153–154° |
| 75 | Cl | Cl | 3-pyridyl-N—oxide | m.p. 180–182° |
| 76 | Cl | Cl | 2-methyl-pyrid-4-yl | |
| 77 | Cl | Cl | 3-methyl-pyrid-5-yl | |
| 78 | Cl | Cl | 2,6-dimethoxypyrid-4-yl | |
| 79 | Cl | Cl | 5-nitropyrid-3-yl | |
| 80 | Cl | Cl | 5-aminopyrid-3-yl | |
| 81 | Cl | Cl | 2-pyridyl-N—oxide | m.p. 172° |
| 82 | Cl | Cl | 5-methylcarbamoylpyrid-3-yl | |
| 83 | Cl | Cl | 5-dimethylaminopyrid-3-yl | |
| 84 | Cl | Cl | 2-chloropyrid-4-yl | |
| 85 | Cl | Cl | 2-isopropylaminopyrid-4-yl | |
| 86 | Cl | Cl | 2-pyrimidyl | m.p. 150–152° |
| 87 | Cl | Cl | 4,6-dimethylpyrimidin-2-yl | m.p. 178–180° |
| 88 | Br | Br | 4,6-dimethylpyrimidin-2-yl | |

TABLE 1-continued

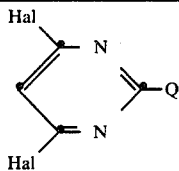

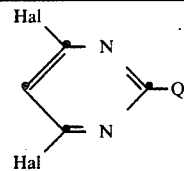

| No. | Hal | | Q | physical data (°C.) |
|---|---|---|---|---|
| 89 | Cl | Cl | 2-chloropyrimidin-4-yl | m.p. 117–118° |
| 90 | Cl | Cl | 2-dimethylaminopyrimidin-4-yl | |
| 91 | Cl | Cl | 4-methoxy-6-methylpyrimidin-2-yl | |
| 92 | Cl | Cl | 2-hydroxy-6-methylpyrimidin-2-yl | |
| 93 | Cl | Cl | 2-chloro-6-methylpyrimidin-2-yl | |
| 94 | Br | Br | 2-chloro-6-methylpyrimidin-2-yl | |
| 95 | Cl | Cl | 2-ethylpyrimidin-5-yl | |
| 96 | Cl | Cl | 2-ethynylpyrimidin-5-yl | |
| 97 | Br | Br | 2-pyrimidinyl | |
| 98 | I | I | 2-pyrimidinyl | |
| 99 | Cl | Cl | 2-pyrazinyl | m.p. 138–142° |
| 100 | Cl | Cl | 2-carbomethoxypyrazin-5-yl | |
| 101 | Br | Gr | 2-methylthiopyrazin-5-yl | |
| 102 | Cl | Cl | 2-chloropyrazin-5-yl | |
| 103 | Cl | Cl | 3-pyridazinyl | |
| 104 | Cl | Cl | 6-methylpyridazin-3-yl | |
| 105 | Cl | Cl | 6-methoxypyridazin-3-yl | |
| 106 | Cl | Cl | 6-chloropyridazin-3-yl | m.p. 148–151° |
| 107 | Cl | Cl | 4-pyridazinyl | |
| 108 | Br | Br | 5-chloropyridazin-3-yl | |
| 109 | Br | Br | 4-pyridazinyl | |
| 110 | Br | Br | 3-pyridazinyl | |
| 111 | Cl | Cl | 4,6-dimethoxy-1,3,5-triazin-2-yl | |
| 112 | Cl | Cl | 4-ethyl-6-methoxy-1,3,5-triazin-2-yl | |
| 113 | Cl | Cl | 4-ethynyl-6-methoxy-1,3,5-triazin-2-yl | |
| 114 | Cl | Cl | 5,6-dimethyl-1,2,4-triazin-3-yl | |
| 115 | Cl | Cl | 1,2,4-triazin-3-yl | |
| 116 | Br | Br | 1,2,4-triazin-3-yl | |
| 117 | Cl | Cl | 3-methyl-1,2,4-triazin-5-yl | |
| 118 | Cl | Cl | 1,2,3-triazin-4-yl | |
| 119 | Cl | Cl | 4-chloro-4-methylpiperidin-6-yl | |
| 120 | Cl | Cl | 5-methylpyridazin-3-yl-N—oxide | |
| 121 | F | Cl | 5-methylpyridazin-3-yl-N—oxide | |
| 122 | Cl | Cl | 1,4-2H—oxazin-5-yl | |
| 123 | Cl | Cl | 1,3-6H—oxazin-2-yl | |
| 124 | Cl | Cl | 1,2,4-thioxahin-3-yl | |
| 125 | Cl | Cl | 1,2,4-oxdiazin-3-yl | |
| 126 | Cl | Cl | 2-benzofuranyl | |
| 127 | Cl | Cl | 6-benzofuranyl | |
| 128 | Cl | Cl | 2-benzothienyl | |
| 129 | Cl | Cl | 5-benzothienyl | |
| 130 | Cl | Cl | 5-benzothiazolyl | |
| 131 | Cl | Cl | 1-methylindol-3-yl | m.p. 179–181° |
| 132 | Cl | Cl | 3-indolyl | |
| 133 | Br | Br | 3-indolyl | |
| 134 | Cl | Cl | 1-methylindol-5-yl | |
| 135 | Cl | Cl | 1,3-benzoxazol-2-yl | |
| 136 | Cl | Cl | 1,2-benzoxazol-5-yl | |
| 137 | Cl | Cl | 6-isobenzofuranyl | |
| 138 | Cl | Cl | 2-methylisoindol-5-yl | |
| 139 | Cl | Cl | 2-methyisoindol-1-yl | |
| 140 | Cl | Cl | 1-isoindolyl | |
| 141 | Br | Br | 1-isoindolyl | |
| 142 | F | Cl | 1-isoindolyl | |
| 143 | Cl | Cl | 6-indazolyl | |
| 144 | Br | Br | 6-indazolyl | |
| 145 | Cl | Cl | 3-ihinolyl | m.p. 183–185° |
| 146 | Br | Br | 6-isochinolyl | |
| 147 | Cl | Cl | 6-fluoroisoquinolin-3-yl | |
| 148 | Cl | Cl | 6-isoquinolyl | |
| 149 | Cl | Cl | 6-quinoxalinyl | m.p. 155° (decomp.) |
| 150 | Cl | Cl | 2-methoxyquinoxalin-7-yl | |
| 151 | Cl | Cl | 2-methoxyquinoxalin-6-yl | |
| 152 | Cl | Cl | 4-quinoxalinyl | |
| 153 | Br | Br | 4-quinoxalinyl | |
| 154 | Cl | Cl | 2-quinoxalinyl | |
| 155 | Cl | Cl | 3-cinnolinyl | |
| 156 | Cl | Cl | 4-methoxyquinazolin-2-yl | |
| 157 | Cl | Cl | 7-carboxylquinoxalin-2-yl | |
| 158 | Br | Br | 1-naphthyl | |
| 159 | Cl | Cl | 2-naphthyl | |
| 160 | Br | Br | 2-naphthyl | m.p. 180–183° |
| 161 | Cl | Cl | 5-chloronaphth-2-yl | |
| 162 | Cl | Cl | 4-methoxynaphth-2-yl | |
| 163 | Cl | Cl | 6-sulfurylnaphth-2-yl | |
| 164 | Cl | Cl | 6-sulfamoylnaphth-2-yl | |
| 165 | F | Cl | 2-naphthyl | |
| 166 | F | F | 2-naphthyl | |
| 167 | Cl | Cl | 3-chromenyl | |
| 168 | Cl | Cl | 3-chromanyl | |
| 169 | Cl | Cl | 6-methoxycarbonylquinoxal-2-yl | |
| 170 | Cl | Cl | 5-chloro-2-methoxypyrid-3-yl | m.p. 166–172° |

TABLE 2

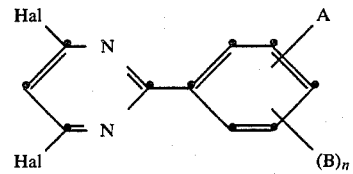

| No. | A | B | Hal | | physical data (°C.) |
|---|---|---|---|---|---|
| 171 | 4-phenylethyl- | H | Cl | Cl | |
| 172 | 4-styryl- | H | Cl | Cl | m.p. 155–157° |
| 173 | 4-(β-phenylethynyl)- | H | Cl | Cl | m.p. 143–145° |
| 174 | 4-(β-4′-chlorophenylethynyl)- | H | Cl | Cl | |
| 175 | 3-(β-phenylethynyl)- | H | Cl | Cl | |
| 176 | 3-(β-3′-methoxyphenylethenyl)- | H | Cl | Cl | |
| 177 | 3-benzyl- | H | Cl | Cl | |
| 178 | 3-(β-phenylethynyl)- | 5-OCH₃ | Cl | Cl | |
| 179 | 4-(β-pyrimidin-2-yl-ethynyl)- | H | Cl | Cl | |
| 180 | 4-(β-pyrimidin-2-ylethyl)- | H | Cl | Cl | |
| 181 | 4-(2′-cyanoethenyl)- | H | Cl | Cl | |
| 182 | 4-(2′-carboxyethenyl)- | H | Br | Br | |
| 183 | 4-(2′-methoxycarbonylethenyl)- | H | Cl | Cl | |

TABLE 2-continued

[Structure: pyrimidine ring with two Hal substituents connected via =N- linkage to phenyl ring with substituent A and (B)$_n$]

| No. | A | B | Hal | | physical data (°C.) |
|---|---|---|---|---|---|
| 184 | 4-(2'-n-butoxycarbonylethenyl)- | H | Cl | Cl | |
| 185 | 4-(2'-carbamoylethenyl)- | H | Cl | Cl | |
| 186 | 4-(2'-carboxy-2'-cyanoethenyl)- | H | Cl | Cl | m.p. 240° (decomp.) Example 5 |
| 187 | 4-(2'-cyano-2'-methoxycarbonylethenyl) | H | Br | Br | |
| 188 | 3-(2'-cyanoethenyl)- | H | Cl | Cl | |
| 189 | 3-(2'-dimethylcarbamoylethenyl)- | H | Cl | Cl | |
| 190 | 4-styrylcarbonyl- | H | Cl | Cl | |
| 191 | 3-(β-pyrid-2-yl-ethenyl-carbonyl)- | H | Cl | Cl | |
| 192 | 4-phenyl- | H | Cl | Cl | m.p. 111–112° |
| 193 | 4-(pyrimidin-2-yl)- | H | Cl | Cl | m.p. 215–218° |
| 194 | 3-(s-triazinyl)- | H | Cl | Cl | |
| 195 | 4-(imidazol-2-yl)- | H | Cl | Cl | |
| 196 | 3-(thiazol-2-yl)- | H | Cl | Cl | |
| 197 | 4-(s-triazinyl)- | H | Cl | Cl | |
| 198 | 3-(thiazol-2-yl)- | H | Br | Br | |
| 199 | 4-phenoxy- | H | Cl | Cl | m.p. 103–105° |
| 200 | 3-phenoxy- | H | Cl | Cl | m.p. 91–93° |
| 201 | 3-(4'-chlorophenoxy)- | H | Cl | Cl | m.p. 105–107° |
| 202 | 4-phenylthio- | H | Cl | Cl | |
| 203 | 4-anilidosulfonyl- | H | Cl | Cl | |
| 204 | 3-anilidosulfonyl- | H | Cl | Cl | |
| 205 | 4-(2'-methoxyethylsulfamoyl)- | H | Cl | Cl | |
| 206 | 4-benzylimino-benzylidenimino- | H | Cl | Cl | m.p. 190° (decomp.) Example 2 |
| 207 | 3-benzylimino- | H | Cl | Cl | m.p. 152–154° |
| 208 | 4-thiophen-2-ylmethylenimino- | H | Cl | Cl | |
| 209 | 4-furfurylimino- | H | Cl | Cl | |
| 210 | 4-(pyrid-2-ylmethylenimino)- | H | Cl | Cl | |
| 211 | 4-(3'-nitrobenzylimino)- | H | Cl | Cl | |
| 212 | 4-(dimethylaminomethylenimino)- | H | Cl | Cl | m.p. 147–149° |
| 213 | 4-(n-butylaminomethylenimino)- | H | Cl | Cl | |
| 214 | 4-(1'-ethylaminoethylenimino)- | H | Cl | Cl | |
| 215 | 3-(dimethylaminomethylenimino)- | H | Cl | Cl | m.p. 100–102° |
| 216 | 3-(isopropylaminomethylenimino)- | H | Cl | Cl | m.p. 119–120° |
| 217 | 4-pyrrol-(1)-yl | H | Cl | Cl | m.p. 150–151° |
| 218 | 3-pyrrol-(1)-yl | H | Cl | Cl | |
| 219 | 4-pyrrol-(1)-yl | 3-CH$_3$ | Cl | Cl | |
| 220 | 3-pyrrol-(1)-yl | 5-OCH$_3$ | Cl | Cl | |
| 221 | 4-pyrazol-1-yl- | H | Cl | Cl | |
| 222 | 3-pyrazol-1-yl- | H | Cl | Cl | |
| 223 | 3-pyrazol-1-yl- | H | Br | Br | |
| 224 | 4-(3'-methyl-1',2',4'-triazol-1-yl)- | H | Cl | Cl | |
| 225 | 3-(5'-chloro-3-methyl-pyrazol-2-yl)- | H | Cl | Cl | |
| 226 | -3,4-methylenedioxy- | | Cl | Cl | m.p. 148–150° Example 1 |
| 227 | -3,4-propylene- | | Cl | Cl | m.p. 120–123° |
| 228 | -3,4-carbonyldioxy- | | Cl | Cl | |
| 229 | -3,4-carbonyldioxy- | | Br | Br | |
| 230 | -2,3-methylenedioxy- | | Cl | Cl | |
| 231 | -3,4-ethylenedioxy- | | Br | Br | |
| 232 | -3,4-methylenecarbonylimido- | | Cl | Cl | |
| 233 | -3,4-methylenecarbonylimido- | | Cl | Cl | |
| 234 | -3,4-methylene-N—methylcarbamoyl- | | Cl | Cl | |
| 235 | -3,4-N,N'—ureido- | | Cl | Cl | |
| 236 | -3,4-carbonylimidocarbonyl- | | Cl | Cl | |
| 237 | -3,4-carbonyl-N—methylimidocarbonyl- | | Cl | Cl | |
| 238 | -3,4-sulfonylimidocarbonyl- | | Cl | Cl | |
| 239 | -3,4-sulfonyl-N—methylimidocarbonyl- | | Cl | Cl | |
| 240 | -3,4-propylenimino- | | Cl | Cl | |
| 241 | -3,4-iminoethylene- | | Cl | Cl | |
| 242 | 2,3-ethylenedioxy | | Cl | Cl | |
| 243 | 4-(2'-hydroxyisopropylamino)- | H | Cl | Cl | wax |
| 244 | 4-(2'-hydroxypropylamino)- | H | Cl | Cl | wax |
| 245 | 4-(2'-hydroxyethylamino)- | H | Cl | Cl | |
| 246 | 4-Di(2'-hydroxyethyl)amine | H | Cl | Cl | m.p. 169–171° Example 4 |
| 247 | 4-(2'-methoxyethylamino)- | H | Cl | Cl | |

TABLE 2-continued

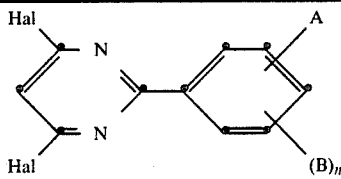

| No. | A | B | Hal | | physical data (°C.) |
|---|---|---|---|---|---|
| 248 | 4-(2',2'-diethylaminoethyl)- | H | Cl | Cl | |
| 249 | 4-(2'-methylthioethylamino)- | H | Cl | Cl | |
| 250 | 4-(2'-chloroethylamino)- | H | Cl | Cl | |
| 251 | 4-Di(2'-methoxyethyl)amino- | H | Cl | Cl | |
| 252 | 4-(N—methyl-N—hydroxyethyl)amino- | H | Cl | Cl | |
| 253 | 4-(2'-methoxypropyl)amino- | H | Cl | Cl | |
| 254 | 4-(N—methyl-3'-pyrrolidinopropyl)amino | H | Cl | Cl | |
| 255 | 4-anilino- | H | Cl | Cl | |
| 256 | 4-p-bromobenzylamino- | H | Cl | Cl | |
| 257 | 4-(pyrid-2-yl)amino- | H | Cl | Cl | |
| 258 | 4-N—benzyl-N—methylamino- | H | Cl | Cl | |
| 259 | 4-N—benzyl-N—methylamino- | H | Br | Br | |
| 260 | 4-phenacetylamino- | H | Cl | Cl | |
| 261 | 4-benzoylamido- | H | Cl | Cl | m.p. 198–200° Example 3 |
| 262 | 4-N—methylbenzoylamido- | H | Cl | Cl | |
| 263 | 4-p-nitrobenzoylamido- | H | Cl | Cl | |
| 264 | 4-(2''-hydroxyethyl)amino- | 3-CH$_3$ | Cl | Cl | |
| 265 | 4-benzoylamido- | 3 Cl | Cl | Cl | |
| 266 | 4-phenoxycarbonylamido- | H | Cl | Cl | |
| 267 | 4-(3'-chlorophenoxycarbonylamido)- | H | Cl | Cl | |
| 268 | 4-phenylureido- | H | Cl | Cl | |
| 269 | 3-(2'hydroxyethylamino)- | H | Cl | Cl | |
| 270 | 3-(2'-ethoxyethylamino)- | H | Cl | Cl | |
| 271 | 3-(2'-dimethylaminoethylamino)- | H | Cl | Cl | |
| 272 | 3-(N—methyl-N—n-propylthiopropyl)amino- | H | Cl | Cl | |
| 273 | 3-(2'-hydroxycyclohexylamino)- | H | Cl | Cl | |
| 274 | 3-(2'-hydroxy-1'-methylpropylamino)- | H | Cl | Cl | |
| 275 | 3-(2'-hydroxy-1'-methylpropylamino)- | H | Br | Br | |
| 276 | 3-anilino- | H | Br | Br | |
| 277 | 3-N—methylanilino- | H | Cl | Cl | |
| 278 | 3-(3-trifluoromethylanilino)- | H | Cl | Cl | |
| 279 | 3-(3-trifluoromethylanilino)- | H | F | F | |
| 280 | 3-pyrimidin-2-yl | H | Br | Br | |
| 281 | 3-benzylamino- | H | Cl | F | |
| 282 | 3-phenacetylamino- | H | Cl | Cl | |
| 283 | 3-benzoylamido- | H | Cl | Cl | |
| 284 | 3-N—isopropylbenzoylamido- | H | Cl | Cl | |
| 285 | 3-benzoylamido- | 3-CH$_3$ | Cl | Cl | |
| 286 | 3-benzoylamido- | 3-CH$_3$ | Br | Br | |
| 287 | 3-(2'-hydroxyethylamino)- | 5-NO$_2$ | Cl | Cl | |
| 288 | 3-(2'-hydroxyethylamino)- | 5-NH$_2$ | Cl | Cl | |
| 289 | 3-phenoxycarbonylamido- | H | Cl | Cl | |
| 290 | 3-phenoxycarbonylamido- | H | Br | Br | |
| 291 | 3-phenylureido- | H | Cl | Cl | |
| 292 | 3-imidazol-1-ylcarbonylamido- | H | Cl | Cl | |
| 293 | 4-benzoyloxy- | H | Cl | Cl | |
| 294 | 4-p-chlorobenzoyloxy- | H | Cl | Cl | |
| 295 | 4-pyrid-(3)-yl-carbonyl-oxy- | H | Cl | Cl | |
| 296 | 3-benzoyloxy- | H | Cl | Cl | |
| 297 | 3-(3'-nitrobenzoyloxy)- | H | Cl | Cl | |
| 298 | 4-benzyloxy- | H | Cl | Cl | |
| 299 | 4-benzyloxy- | H | Br | Br | |
| 300 | 3-benzyloxy- | H | Cl | Cl | |
| 301 | 3'-phenoxypropylenoxy- | H | Cl | Cl | m.p. 162–103° |
| 302 | 4-N—methylcarbamoyloxy- | H | Cl | Cl | m.p. 205–209° |
| 303 | 3-N—methylcarbamoyloxy- | H | Cl | Cl | m.p. 134–137° |
| 304 | 4-N—methoxy-N—methylcarbamoyloxy | H | Cl | Cl | m.p. 172–174° |
| 305 | 4-N—phenylcarbamoyloxy- | H | Cl | Cl | m.p. 180–186° |
| 306 | 4-N—n-butylcarbamoyloxy- | H | Cl | Cl | m.p. 142–144° |
| 307 | 4-p-chlorophenylcarbamoyloxy- | H | Cl | Cl | m.p. 195–198° |
| 308 | 4-N,N—dimethylcarbamoyloxy- | H | Cl | Cl | m.p. 191–193° |
| 309 | 3-N—phenylcarbamoyloxy- | H | Cl | Cl | m.p. 167–170° |
| 310 | 3-N—methoxy-N—methylcarbamoyloxy | H | Cl | Cl | |
| 311 | 3-N—methyl-N—phenylcarbamoyloxy | H | Cl | Cl | |
| 312 | 3-N—ethylcarbamoyloxy- | H | Cl | Cl | |
| 313 | 3-N—m-chlorophenylcarbamoyloxy- | H | Cl | Cl | |
| 314 | 2-N—methylcarbamoyloxy- | H | Cl | Cl | |
| 315 | 4-methylsulfonato | H | Cl | Cl | m.p. 144–147° |
| 316 | 4-p-tolylsulfonato- | H | Cl | Cl | |
| 317 | 3-methylsulfonato- | H | Cl | Cl | |

TABLE 2-continued

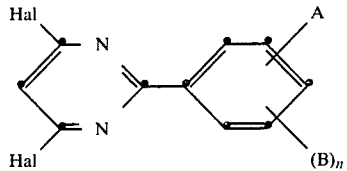

| No. | A | B | Hal | | physical data (°C.) |
|---|---|---|---|---|---|
| 318 | 3-phenylsulfonato- | H | Cl | Cl | |
| 319 | 4-methylsulfonamido- | H | Cl | Cl | |
| 320 | 4-trifluoromethylsulfonamido- | H | Cl | Cl | |
| 321 | 4-methylsulfonyl-N—methylamido- | H | Cl | Cl | |
| 322 | 3-methylsulfonamido- | H | Cl | Cl | |
| 323 | 3-p-tolylsulfonamido- | H | Cl | Cl | |
| 324 | 4-p-tolylsulfonamido- | H | Cl | Cl | |
| 325 | 4-N—methoxy-N—methylcarbamoyloxy | H | Br | Cl | m.p. 170-171° |
| 326 | 4-(β-4'-methoxybenzylimino)- | H | Cl | Cl | m.p. 150° |
| 327 | 4-(β-4'-nitrobenzylimino)- | H | Cl | Cl | m.p. 226° |

FORMULATION EXAMPLES

The compounds of formula I are normally not used by themselves in agriculture. They are used in the form of ready for use formulations which can be applied either direct or diluted with water.

EXAMPLE 9

Dusts: The followwing ingredients are used to formulate (a) 5% and b) a 2% dust:

(a)

5 parts of 4,6-dichloro-2-(3-thienyl)pyrimidine or a mixture thereof with 2-chloro-2',6'-diethyl-N-(butoxymethyl)acetanilide, 95 parts of talc;

(b)

2 parts of the above compound or mixture, 1 part of highly dispersed silicic acid 97 parts of talc.

The active ingredients are mixed with the carriers and ground and in this form can be processed to dusts for application.

EXAMPLE 10

Granulate: The following substances are used to formulate a 5% granulate:

5 parts of 4,6-dichloro-2-(1-naphthyl)pyrimidine or a mixture thereof with 2-chloro-2',6'-diethyl-N-(methoxymethyl)acetanilide,
0.25 part of epichlorohydrin
0.25 part of cetyl polyglycol ether
3.25 parts of polyethylene glycol
91 parts of kaolin (particle size 0.3-0.8 mm).

The active ingredient or mixture is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo.

EXAMPLE 11

Wettable powders: The following constituents are used to formulate (a) a 70%, (b) a 40%, (c) and (d) a 25% ad (e) a 10% wettable powder:

(a)

70 parts of 4,6-dichloro-2-(2-furyl)pyrimidine or a mixture thereof with 2-chloro-2',6'-diethyl-N-(2"-propoxyethyl)acetanilide,
5 parts of sodium dibutylnaphthylsulfonate
3 parts of napthalenesulfonic acid/phenolsulfonic acid/-formaldehyde condensate (3:2:1)
10 parts of kaolin
12 parts of Champagne chalk (b)

40 parts of the above compound or mixture
5 parts of sodium lignosulfonate
1 part of sodium dibutylnaphthalenesulfonic acid
54 parts of silicic acid (c)

25 parts of the above compound or mixture
4.5 parts of calcium lignosulfate
1.9 parts of Champagne chalk/hydroxyethyl cellulose mixture (1:1)
1.5 parts of sodium dibutylnaphthalenesulfonate
19.5 parts of silicic acid
19.5 parts of Champagne chalk
28.1 parts of kaolin (d)

25 parts of the above compound or mixture
2.5 parts of isooctylphenoxy polyethylene ethanol
1.7 parts of a Champagne chalk/hydroxyethyl cellulose mixture (1:1)
8.3 parts of sodium aluminium silicate
16.5 parts of kieselguhr
46 parts of kaolin (e)

10 parts of the above compound or mixture
3 parts of a mixture of the sodium salts of saturated fatty alcohol sulfates
5 parts of naphthalenesulfonic acid/formaldehyde condensate
82 parts of kaolin.

The active ingredients are intimately mixed in suitable mixers with the additives and ground in appropriate mills and rollers. Wettable powders of excellent wettability and suspension power are obtained. These wettable powders can be diluted with water to give suspensions of the desired concentration and can be used in particular for foliar application (for growth inhibition or fungicidal application).

EXAMPLE 12

Emulsifiable concentrate: The following ingredients are mixed to formulate a 25% emulsifiable concentrate:
25 parts of 4,6-dichloro-2-(1-pyrroly)pyrimidine or a mixture thereof with 2-chloro-6'-ethyl-N-(2''-methoxy-1''-methyl-ethyl)acet-o-toluidide,
10 parts of a mixture of an alkyarylsulfonate and a fatty alcohol polyglycol ether,
5 parts of dimethylformamide
57.5 parts of xylene.

EXAMPLE 13

Paste: The following ingredients are used to formulate a 45% paste:

(a)

45 parts of 4,6-dichloro-2-(2-pyridyl)pyrimidine or a mixture thereof with 2-chloro-2',6'-diethyl-N-(methoxymethyl)acetanilide,
5 parts of sodium aluminium silicate,
14 parts of cetyl polyethylene glycol ether with 8 moles of ethylene oxide,
3 parts of oleyl polyethylene glycol ether with 5 moles of ethylene oxide,
2 parts of spindle oil,
10 parts of polyethylene glycol,
23 parts of water.

(b)

45 parts of the above compound or mixture,
5 parts of ethylene glycol,
3 parts of octylphenoxy polyethylene glycol containing 9-10 moles of ethylene oxide per mole of octylphenol,
3 parts of a mixture of aromatic sulfonesulfonic acids, condensed with formaldehyde as ammonium salt,
1 part of silicone oil in form of a 75% emulsion,
0.1 part of a mixture of 1-(3-chloroallyl)-3,5,7-triazoazonium-adamantane chloride with sodium carbonate (chloride value at least 11.5%),
0.2 part of a biopolymeric thickener containing a maximum of 100 bacilli per gram,
42.7 parts of water The active ingredient is intimately mixed with the adjuvants in appropriate devices and ground. By diluting the resultant paste with water, it is possible to prepare suspension of the desired concentration.

BIOLOGICAL EXAMPLES

The ability of the compounds of formula I to protect cultivated plants from the phytotoxic effects of potent herbicides is illustrated in the following Examples. In the test procedures, the compounds of formula I are referred to as safeners. The relative protective action is expressed in percent, with 0% denoting the action of the herbicide when applied alone and 100% denoting the intended normal growth of the plant.

EXAMPLE 14

Test with safener and herbicide in rice sown in water. Application of the antidote during immersion of the rice seeds.

Rice seeds are immersed for 48 hours in 100 ppm solutions of the compound for testing as safener. The seeds are then allowed to dry for about 2 hours until they are no longer tacky. Plastic containers measuring 25 cm×17 cm ×12 cm are filled with sandy loam to 2 cm below the edge. The pretreated seeds are sown on the surface of the soil in the containers and only lightly covered. The soil is kept in a moist (non-marshy) state. Then a dilute solution of the herbicide is sprayed onto the surface of the soil. The water level is then gradually raised in accordance with growth of the rice plants. The relative protective action of the safener is evaluated (in %) 21 days after aplication. The plants treated with herbicide alone (no protective action) and the completely untreated controls (100% growth) are used for reference purposes. The results are reported in the table below.

HERBICIDE 2-chloro-2',6'-diethyl-N-(2''-propylethyl)acetanilide ("pretilachlor"). Rate of application: 0.25 kg/ha.

| Compound No. | relative protective action % | Compound No. | relative protective action % |
| --- | --- | --- | --- |
| 1 | 50 | 170 | 12.5 |
| 2 | 38 | 173 | 12.5 |
| 3 | 38 | 192 | 25 |
| 4 | 75 | 193 | 12.5 |
| 5 | 63 | 199 | 38 |
| 7 | 38 | 206 | 50 |
| 14 | 63 | 207 | 63 |
| 16 | 50 | 212 | 50 |
| 26 | 50 | 215 | 63 |
| 62 | 63 | 217 | 25 |
| 66 | 63 | 218 | 12.5 |
| 69 | 63 | 226 | 38 |
| 71 | 63 | 243 | 38 |
| 72 | 25 | 244 | 38 |
| 74 | 25 | 246 | 12.5 |
| 75 | 38 | 302 | 50 |
| 81 | 12.5 | 303 | 63 |
| 86 | 25 | 304 | 63 |
| 87 | 25 | 305 | 63 |
| 89 | 12.5 | 306 | 38 |
| 90 | 12.5 | 307 | 50 |
| 99 | 38 | 308 | 12.5 |
| 106 | 63 | 309 | 38 |
| 145 | 38 | 325 | 50 |
| 159 | 38 | 326 | 50 |

EXAMPLE 15

Test with safener and herbicide in rice. Preemergence application of safener and herbicide as tank mixture.

Rice seeds are soaked for 48 hours in water. Plastic containers measuring 25 cm×17 cm×12 cm are filled with soil into which the soaked seeds are sown. The compound for testing as safener and the herbicide are then sprayed together as tank mixture onto the surface of the soil. The water level is raised gradually in accordance with the growth of the rice plants. The protective action of the safener is evaluated in percent 18 days after transplantation. The plants treated with herbicide alone (no protective action) as well as the completely untreated controls (100% relative protective action) serve as references for the evaluation. The results are reported in the following table.

HERBICIDE 2-chloro-2',6'-diethyl-N-(2''-propoxyethyl)-acetanilide "pretilachlor"

| Safener Compound | Rate of application in kg/ha | Herbicide in kg/ha | relative protective action in % |
|---|---|---|---|
| 1 | 1 | 1 | 63 |
| 1 | 0.5 | 0.5 | 63 |
| 2 | 1 | 1 | 75 |
| 2 | 0.5 | 0.5 | 63 |
| 5 | 1 | 1 | 25 |
| 5 | 0.5 | 0.5 | 75 |
| 14 | 1 | 1 | 38 |
| 14 | 0.5 | 0.5 | 63 |
| 16 | 1 | 1 | 38 |
| 16 | 0.5 | 0.5 | 63 |
| 69 | 1 | 1 | 63 |
| 69 | 0.5 | 0.5 | 63 |
| 75 | 1 | 1 | 63 |
| 75 | 0.5 | 0.5 | 75 |
| 99 | 1 | 1 | 63 |
| 99 | 0.5 | 0.5 | 75 |
| 215 | 1 | 1 | 25 |
| 215 | 0.5 | 0.5 | 38 |
| 226 | 1 | 1 | 38 |
| 226 | 0.5 | 0.5 | 38 |
| 302 | 1 | 1 | 25 |
| 302 | 0.5 | 0.5 | 50 |
| 303 | 1 | 1 | 38 |
| 303 | 0.5 | 0.5 | 63 |
| 305 | 1 | 1 | 25 |
| 305 | 0.5 | 0.5 | 38 |
| 325 | 1 | 1 | 12.5 |
| 325 | 0.5 | 0.5 | 38 |

EXAMPLE 16

Tests with safener and herbicide in transplanted rice. Preemergence application of safener and herbicide as tank mixture. Rice plants are reared in soil to the 1½-to 2-leaf stage. The plants are then transplanted in bunches (always 3 plants together) into sandy loam in containers measuring 47 cm×29 cm×24 cm. The surface of the soil is then covered with water to a height of 1.5 to 2 cm. Two to three days after transplantation, the herbicide and the safener as test composition are applied together direct to the water as tank mixture. The protective action of the safener is evaluated in percent 24 days after transplantation. The plants treated with herbicide alone (no protective action) as well as the completely untreated controls (100% protective action) serve as references for the evaluation. The results are reported below.

HERBICIDE 2-chloro-2',6'-diethyl-N-(2'-propoxyehtyl)-acetanilide "pretilachlor"

| Safener Compound No. | Rate of application in kg/ha | Herbicide in kg/ha | relative protective action in % |
|---|---|---|---|
| 1 | 1 | 1 | 25 |
| 1 | 0.5 | 1 | 25 |
| 1 | 0.75 | 0.75 | 12.5 |
| 1 | 0.375 | 0.75 | 12.5 |
| 69 | 1 | 1 | 38 |
| 69 | 0.5 | 1 | 25 |
| 69 | 0.75 | 0.75 | 38 |
| 69 | 0.375 | 0.75 | 25 |
| 75 | 1 | 1 | 25 |
| 75 | 0.5 | 1 | 25 |
| 75 | 0.75 | 0.75 | 38 |
| 75 | 0.375 | 0.75 | 38 |
| 215 | 1 | 1 | 12.5 |
| 215 | 0.5 | 1 | 25 |
| 215 | 0.75 | 0.75 | 25 |
| 215 | 0.375 | 0.75 | 25 |
| 226 | 1 | 1 | 12.5 |
| 226 | 0.5 | 1 | 12.5 |
| 226 | 0.75 | 0.75 | 50 |
| 226 | 0.375 | 0.75 | 25 |
| 302 | 1 | 1 | 12.5 |
| 302 | 0.5 | 1 | 12.5 |
| 302 | 0.75 | 0.75 | 25 |
| 302 | 0.375 | 0.75 | 25 |

EXAMPLE 17

Test with safener and herbicide in rice sown dry. Application of the safener as seed dressing.

Rice seeds are mixed with the test safener in a glass container. Seeds and test comound are well mixed by shaking and rotating. Containers measuring 47 cm×29 cm×24 cm are then filled with sandy loam and the dressed seeds are sown therein. The seeds are covered and a dilute solution of the herbicide is then sprayed onto the surface of the soil. About 20 days after sowing, when the rice plants have attained the 3-leaf stage, the surface of the soil is covered with water to a height of 4 cm. The protective action of the safener is evaluated in percent 30 days after application of the herbicide. The plants treated with herbicide alone (no protective action) as well as the completely untreated controls (100% relative protective action) serve as references for the evaluation. The results are as follows:

HERBICIDE 2-chloro-6'-ethyl-N-(2''-methoxy-1''-methylethyl)-acet-o-toluidide ("metolachlor")

| Safener compound No. | Rate of application in kg/ha | Herbicide in kg/ha | relative protective action in % |
|---|---|---|---|
| 1 | 0.5 | 0.5 | 12.5 |
| 1 | 0.5 | 0.25 | 25 |
| 5 | 0.5 | 0.5 | 25 |
| 5 | 0.5 | 0.25 | 25 |
| 14 | 0.5 | 0.5 | 25 |
| 14 | 0.5 | 0.25 | 12.5 |
| 16 | 0.5 | 0.5 | 25 |
| 16 | 0.5 | 0.25 | 38 |
| 69 | 0.5 | 0.5 | 12.5 |
| 69 | 0.5 | 0.25 | 38 |
| 226 | 0.5 | 0.5 | 25 |
| 226 | 0.5 | 0.25 | 38 |
| 302 | 0.5 | 0.5 | 12.5 |
| 302 | 0.5 | 0.25 | 25 |
| 305 | 0.5 | 0.5 | 12.5 |
| 305 | 0.5 | 0.25 | 25 |

EXAMPLE 18

Test with safener and herbicide in dry rice. Application of the antidote as seed dressing.

Rice seeds are mixed with the compound for testing as safener in a glass container. Seeds and safener are well mixed by shaking and rotating. Containers measuring 47 cm×29 cm×24 cm are then filled with sandy loam and the dressed seeds are sown therein. The seeds are covered and the herbicide is then sprayed onto the surface of the soil. The protective action of the safener is evaluated in percent 18 days after sowing. The plants treated with herbicide alone (no protective action) as well as the completely untreated controls (100% relative protective action) serve as references for the evaluation. The results are as follows:

HERBICIDE 2-chloro-6'-ethyl-N-(2''-methoxy-1''-methylethyl)-acet-o-toluidide ("metolachlor")

| Safener Compound No. | Rate of application in k/kg of seeds | Herbicide in kg/ha | relative protective action in % |
|---|---|---|---|
| 1 | 0.5 | 0.5 | 12.5 |
| 1 | 0.5 | 0.25 | 25 |
| 5 | 0.5 | 0.5 | 25 |
| 5 | 0.5 | 0.25 | 38 |
| 14 | 0.5 | 0.5 | 25 |
| 14 | 0.5 | 0.25 | 12.5 |
| 16 | 0.5 | 0.5 | 25 |
| 16 | 0.5 | 0.25 | 38 |
| 69 | 0.5 | 0.5 | 12.5 |
| 69 | 0.5 | 0.25 | 38 |
| 225 | 0.5 | 0.5 | 25 |
| 225 | 0.5 | 0.25 | 38 |
| 302 | 0.5 | 0.5 | 12.5 |
| 302 | 0.5 | 0.25 | 25 |
| 325 | 0.5 | 0.5 | 12.5 |
| 325 | 0.5 | 0.25 | 25 |

EXAMPLE 19

Test with safener and herbicide in sorghum. Preemergence application of herbicide and safener as tank mixture.

Pots (diameter at the top 6 cm) are filled with sandy loam and Funk G 522 sorghum seeds are sown therein. The seeds are covered and a dilute solution of the compound for testing as safener, together with the herbicide, is then sprayed as tank mixture onto the surface of the soil. The protective action of the safener is evaluated (in %) 21 days after application. The plants treated with herbicide alone (no action) and the completely untreated controls (100% protective action) are used for reference purposes. The results are reported below.

HERBICIDE 2-chloro-6'-ethyl-N-(2''-methoxy-1''-methylethyl)-acet-o-toluidide ("metolachlor")

| Safener compound No. | Rate of application in kg/ha | Herbicide in kg/ha | relative protective action in % |
|---|---|---|---|
| 1 | 1.5 | 1.5 | 25 |
| 2 | 1.5 | 1.5 | 25 |
| 145 | 1.5 | 1.5 | 25 |
| 186 | 1.5 | 1.5 | 50 |
| 325 | 1.5 | 1.5 | 38 |
| 326 | 1.5 | 1.5 | 38 |

EXAMPLE 20

Test with safener and herbicide in wheat. Postemergence application of herbicide and antidote as tank mixture.

"Farnese" wheat seeds are sown in plastic pots (diameter at the top 11 cm) containing 0.5 liter of earth in a greenhouse. The seeds are covered and the compound for testing as safener is applied postemergence, together with the herbicide, as tank mixture. The protective action of the safener is evaluated (in %) 20 days after application. The plants treated with herbicide alone (no action) and the completely untreated controls (100% relative protective action) are used for reference purposes. The results are reported below:

HERBICIDE propynyl α-[3-(2,4-dichloropyridyl-2-oxy)phenoxy]-propionate ("chlorazifor-propynyl")

| Safener Compound No. | Rate of application in kg/ha | Herbicide in kg/ha | relative protective action in % |
|---|---|---|---|
| 5 | 1.5 | 0.75 | 25 |
| 62 | 1.5 | 0.75 | 63 |
| 106 | 1.5 | 0.75 | 63 |
| 145 | 1.5 | 0.75 | 63 |
| 217 | 1.5 | 0.75 | 50 |
| 261 | 1.5 | 0.75 | 25 |

EXAMPLE 21

Test with safener and herbicide in soybeans. Preemergence application of safener and herbicide as tank mixture.

Plastic containers measuring 25 cm×17 cm×12 cm are filled with sany loam and soybean seeds of the "Hark" variety are sown therein. The seeds are covered and a dilute solution of the test safener together with the herbicide is then sprayed as tank mixture onto the surface of the soil. Evaluation of the protective action of the safener in percent is made 30 days after the application. The plants treated with herbicide alone (no protective action) as well as the completely untreated controls (100% relative protective action) serve as references for the evaluation. The result is as follows:

HERBICIDE 4-amino-6-tert-butyl-4,5-dihydro-3-methylthio-1,2,4-triazin-S-one ("metribuzin").

| Safener Compound No. | Rate of application in kg/ha | Herbicide in kg/ha | relative protective action in % |
|---|---|---|---|
| 199 | 1.5 | 0.75 | 25 |

What is claimed is:

1. A composition for protecting cultivated plants from damage by herbicides, which cmposition contains a plant-protecting effective amount of a 2-phenylpyrimidine, a 2-naphthylpyrimidine or a 2-heterocyclylpyrimidine of the formula

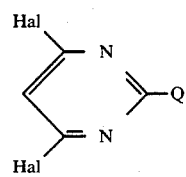

wherein Q is

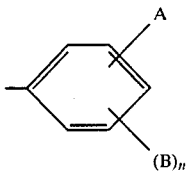

a naphthyl group or a heterocyclic ring which is furan, pyran, thiophene, thiazole, pyridine, pyrroline, oxazole, isoxazole, thioxazole, isothiazole, thiadiazole, oxthiazole, pyrrole, imidazole, pyrazole, pyrazine, pyrimidine, pyridazine, 1,3,5-triazine, 1,2,4,-triazine, 1,2,4-triazole, 1,2,3-triazole, 1,3,4-triazole, oxdiazole, oxazine, furazone, pyridine-N-oxide, thiophene-5-oxide, benzthiophene, benzofuran, pyridine-N-oxide, thiophene-5-oxide, benzthiophene, isobenzofuran, chromene, chroman, indole, isoindole, indazole, quinolin, isoquinoline, phthalazine, quinoxaline, quinazoline, cinnoline, benzthiazole and benzimidazole and which is unsubstituted or substituted by one or two identical or different members selected from halogen, nitro, cyano, $XR_3$, $COOR_3$, $NR_3R_4$, $SO_3H$ or $SO_2NR_3R_4$, $C_1$-$C_6$-alkyl, $C_2$-$C_6$-alkenyl or $C_2$-$C_6$-alkynyl; A is $R_1$, $XR_1$, $COR_1$ or $XCOR_1$, $C_1$-$C_6$alkyl substituted by $R_1$ or $XR_1$, $C_2$-$C_6$alkenyl substituted by cyano, $R_1$, $XR_1$, $COR_1$ or $COR_2$, or is $C_2$-$C_6$alkynyl substituted by $R_1$ or $XR_1$ or is a radical $-OCONR_8R_9$, $OSO_2R_9$ or $-NR_3-SO_2R_9$, X is oxygen, sulfur, or the $-SO_2-$ group, $R_1$ is a phenyl or an unsaturated heterocyclic group which is unsubstituted or substituted by halogen, $C_1$-$C_4$alkyl, $C_1$-$C_4$haloalkyl, nitro, cyano or X-$C_1$-$C_4$— alkyl, $R_2$ is hydrogen, $C_1$-$C_6$alkyl which is unsubstituted or substituted by hydroxy, $C_1$-$C_6$alkoxy, $-COR_2$, $-NR_3R_4$, or is $C_2$-$C_6$alkenyl or $C_2$-$C_6$alkynyl, $R_3$ and $R_4$, each independently of the other, is hydrogen, $C_1$-$C_6$alkyl which is unsubstituted or substituted by hydroxyl, $C_1$-$C_6$alkoxy, $-COR_2$ or $-NR_3R_4$, or is $C_2$-$C_6$alkenyl or $C_2$-$C_6$alkynyl; or $R_3$ and $R_4$ together form a 4 to 6-membered alkylene chain which may be interrupted by oxygen, sulfur, the imino group or a $C_1$-$C_4$alkylimino group; and A is also a radical $-N=CR_1R_5$ or $$-N=C-NR_3R_4,$$
$$\phantom{-N=C}|\phantom{NR_3R_4,}$$
$$\phantom{-N=C}R_6$$

wherein $R_5$ is hydrogen, $C_1$-$C_6$ alkyl which is unsubstituted or substituted by X-$C_1$-$C_6$alkyl, $R_6$ is hydrogen or $C_1$-$C_6$alkyl, or is a pyrryl, piperazyl, imidazolyl of triazolyl radical which is bound through nitrogen and is unsubstituted or substituted by $C_1$-$C_4$alkyl or halogen, or is a radical $-NR_3R_7$ or $R_1$, $R_7$ is a $R_1$, $COR_1$, $XCOR_1$, $C_1$-$C_6$alkyl or $C_3$-$C_6$cycloalkyl group, each substituted by halogen, hydroxyl, $C_1$-$C_6$alkoxy, $C_1$-$C_6$alkylthio, $NR_3R_4$ or $R_1$, or $R_3$ and $R_7$ together form a 4- to 6-membered alkylene chain which may be interrupted by oxygen, sulfur, the imino group or a $C_1$-$C_4$alkylimino group, $R_8$ is hydrogen $C_1$-$C_6$alkyl, $C_3$-$C_6$alkenyl, $C_3$-$C_6$alkynyl, $C_1$-$C_6$ alkoxy, $C_3$-$C_6$alkenyloxy or $C_3$-$C_6$alkynyloxy, $R_9$ has the same meaning as $R_1$ or is $C_1$-$C_4$alkyl, $C_1$-$C_6$haloalkyl, $C_3$-$C_6$alkenyl or $C_3$-$C_6$alkynyl, B is hydrogen, halogen, nitro, cyano, an $XR_2$, $NR_3R_4$, $C_1$-$C_6$alkyl or $C_3$-$C_6$cycloalkyl group each unsubstituted or substituted by halogen or $XR_2$, or is $C_2$-$C_6$alkenyl or $C_2$-$C_6$alkynyl; or A and B together form a 3- or 4-membered chain, the members of which are formed by oxygen, sulfur, a $-CH_2-$, $-CH=$, $-NH-$, $-N(C_1$-$C_4$alkyl$)-$, $CH$-$C_1$-$C_4$alkyl$-$, $-C(C_1$-$C_4)$alkyl$=$, $C(C_1$-$C_4$alkyl$)_2$ or $-CO$ group, with the proviso that two oxyen and/or sulfur atoms are not directly adjacent ring members, n is 0 or 1, and Hal is halogen, together with an inert carrier.

2. A composition of claim 1, which further contains
(a) a chloroacetanilide, triazinone or pyridyloxyphenoxypropionate herbicide.

3. A method of protecting plants of cereal, rice, sorghum or soybean from the harmful action of a herbicide of the classes chloracetanilides, triazinones or pyridyloxy-phenoxy propionates, which comprises the use of an effective amount of a 2-phenylpyrimidine, 2-naphthyl-pyrimidine or 2-heterocyclylpyrimidine of the formula

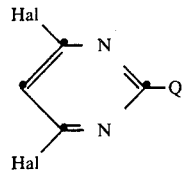

wherein Q is

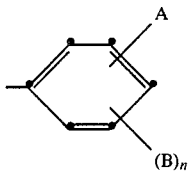

or a heterocyclic ring which is furan, pyran, thiophene, thiazole, pyridine, pyrroline, oxazole, isoxazole, thioxazole, isothiazole, thiadiazole, oxthiazole, pyrrole, imidazole, pyrazole, pyrazine, pyrimidine, pyridazine, 1,3,5-triazine, 1,2,4,-triazine, 1,2,4-triazole, 1,2,3-triazole, 1,3,4-triazole, oxdiazole, oxazine, furazane, pyridine-N-oxide, thiophene-5-oxide, benzthiophene, benzofuran, pyridine-N-oxide, thiophene-5-oxide, benzthiophene, isobenzofuran, chromene, chromane, indole, isoindole, indazole, quinoline, isoquinoline, phthalazine, quinoxaline, quinazoline, cinnoline, benzthiazole and benzimidazole and which is unsubstituted or substituted by one or two of halogen, nitro, cyano, $XR_3$, $COOR_3$, $SO_3H$ or $SO_2NR_3R_4$, $C_1$-$C_6$-alkyl, $C_2$-$C_6$-alkenyl or $C_2$-$C_6$alkynyl;

A is a radical $R_1$, $XR_1$, $COR_1$ or $XCOR_1$, $C_1$-$C_6$-alkyl substituted by $R_1$ or $XR_1$, $C_2$-$C_6$-alkenyl substituted by cyano, $R_1$, $XR_1COR_1$ or $COR_2$, or $C_2$-$C_6$-alkynyl substituted by $R_1$ or $XR_1$, or is a radical $-OCONR_8R_9$, $OSO_2R_9$ or $-NR_3-SO_2R_9$, X is oxygen, sulfur, or the —SO— or —SO$_2$— group, R$_1$ is a phenyl radical or an unsaturated heterocyclic radical which is unsubstituted or substituted by halogen, C$_1$-C$_4$-alkyl, C$_1$-C$_4$-haloalkyl, nitro, cyano or X-C$_1$-C$_4$-alkyl, R$_2$ is hydrogen, C$_1$-C$_6$-alkyl which is unsubstituted or substituted by hydroxy, C$_1$-C$_6$-alkoxy, —COR$_2$, —NR$_3$R$_4$, or is C$_2$-C$_6$-alkenyl or C$_2$-C$_6$-alkynyl, R$_3$ and R$_4$, each independently of the other, is hydrogen, C$_1$-C$_6$-alkyl which is unsubstituted or unsubstituted by hydroxyl, C$_1$-C$_6$-alkoxy, —COR$_2$ or —NR$_3$R$_4$, or is C$_2$-C$_6$-alkenyl or C$_2$-C$_6$-alkynyl; or R$_3$ and R$_4$ together form a 4 to 6-membered alkylene chain which may be interrupted by oxygen, sulfur, the imino group or a C$_1$-C$_4$-alkylimino group; and A is also a radical —N=CR$_1$R$_5$ or

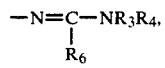

wherein

R$_5$ is hydrogen, C$_1$-C$_6$-alkyl which is unsubstituted or substituted by X-C$_1$-C$_6$-alkyl, R$_6$ is hydrogen or C$_1$-C$_6$-alkyl, or is a pyrryl, piperazyl, imidazolyl or triazolyl radical which is bound through nitrogen and is unsubsituted or substituted by C$_1$-C$_4$-alkyl or halogen, or is a radical —NR$_3$R$_7$ or R$_1$, or R$_7$ is a R$_1$, COR$_1$, XCOR$_1$, C$_1$-C$_6$-alkyl or C$_3$-C$_6$-cycloalkyl group, each substituted by halogen, hydroxyl, C$_1$-C$_6$-alkoxy, C$_1$-C$_6$-alkylthio, —NR$_3$R$_4$ or R$_1$, or R$_3$ and R$_7$ together form a 4- 6-membered alkylene chain which may be interrupted by oxygen, sulfur, the imino group or a C$_1$-C$_4$-alklimino group, R$_8$ is hydrogen C$_1$-C$_6$-alkyl, C$_3$-C$_6$-alkenyl, C$_3$-C$_6$-alkynyl, C$_1$-C$_6$-alkoxy, C$_3$-C$_6$-alkenyloxy or C$_3$-C$_6$-alkynyloxy, R$_9$ has the same meaning as R$_1$ or is C$_1$-C$_4$-alkyl, C$_1$-C$_6$-haloalkyl, C$_3$-C$_6$-alkenyl or C$_3$-C$_6$-alkynyl, B is hydrogen, halogen, nitro, cyano, an XR$_2$, NR$_3$R$_4$, C$_1$-C$_6$-alkyl or C$_3$-C$_6$-cycloalkyl group each unsubstituted or substituted by halogen or XR$_2$, or is C$_2$-C$_6$-alkenyl or C$_2$-C$_6$-alkynyl; or A and B together form a 3- 4-membered chain, the members of which are formed by oxygen, a —CH$_2$—, —CH=, with the proviso that two oxygen atoms are not directly adjacent ring members, n is 0 or 1, and Hal is halogen.

4. A method of protecting plants of cereal, rice sorghum or soybean from damage caused by the application of a herbicide of the classes chloroacetanilides, triazinones or pyridyloxy-phenoxypropionnates which comprises (a) treating the locus of the plant before or during application of the herbicide, or (b) treating the seeds or seedlings of the plant or the plant itself with an effective amount of a 2-phenylpyrimidine, 2-naphthylpyrimidine or 2-heterocyclylpyrimidine of claim 3.

* * * * *